United States Patent [19]
Yanagihara et al.

[11] Patent Number: 5,397,696
[45] Date of Patent: Mar. 14, 1995

[54] PAPUA NEW GUINEA HUMAN T-LYMPHOTROPIC VIRUS

[75] Inventors: Richard Yanagihara; Vivek R. Nerurkar, both of Frederick, Md.; Carol Jenkins, Goroka, Papua New Guinea; Mark Miller, Fort Lee, N.J.; Ralph M. Garruto, Boyds, Md.

[73] Assignee: The United States of America as represented by the Department of Health and Human Services, Washington, D.C.

[21] Appl. No.: 743,518

[22] Filed: Aug. 12, 1991

Related U.S. Application Data

[63] Continuation-in-part of Ser. No. 572,090, Aug. 24, 1990, abandoned.

[51] Int. Cl.⁶ ............................................. C12N 7/02
[52] U.S. Cl. ..................................... 435/5; 435/235.1; 435/7.1; 435/7.2; 435/7.21; 435/7.24; 435/7.92; 435/239
[58] Field of Search .................... 435/5, 7.1, 7.2, 7.21, 435/7.24, 7.92, 235.1, 239, 237

[56] References Cited

PUBLICATIONS

Asher et al: "Ab to HTLV-I in Populations of the Southwestern Pacific" J. of Med Vir 26:339-51 (1988).
Popovic et al "Transformation of Human Umbilical Cord Blood T-cells by HTLV" PNAS 80:5402-6 (1983).
Gallo et al "Comparison of Immunofluorescence, EI, & WB Methods for Detection of Ab to HTLV-1" J. of Clin Microb V26 #8 pp. 1487-1491 (1988).

Primary Examiner—Christine M. Nucker
Assistant Examiner—Jeffrey Stucker
Attorney, Agent, or Firm—Morgan & Finnegan

[57] ABSTRACT

The present invention relates to a human T-cell line (PNG-1) persistently infected with a Papua New Guinea (PNG) HTLV-I variant and to the infecting virus (PNG-1 variant). Cells of the present invention express viral antigens, type C particles and have a low level of reverse transcriptase activity. The establishment of this cell line, the first of its kind from an individual from Papua New Guinea, makes possible the screening of Melanesian populations using a local virus strain. The present invention also relates to vaccines for use in humans against infection with and diseases caused by HTLV-I and related viruses. The invention further relates to a variety of bioassays and kits for the detection and diagnosis of infection with and diseases caused by HTLV-I and related viruses.

5 Claims, 33 Drawing Sheets

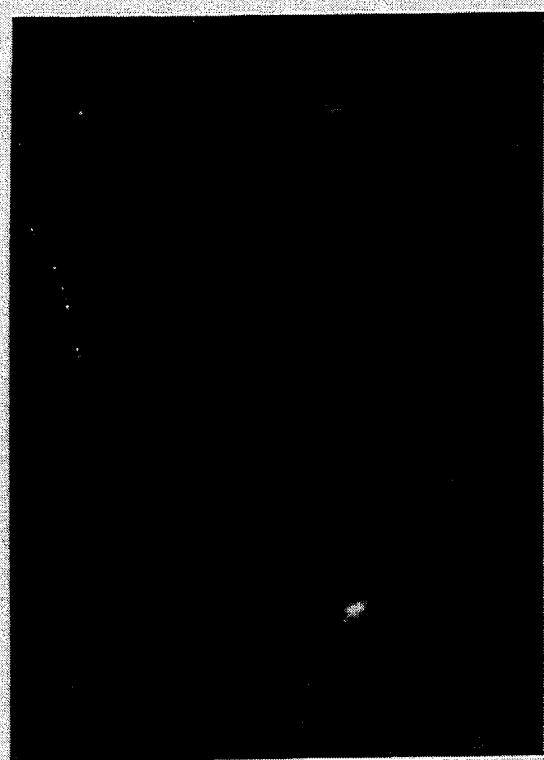 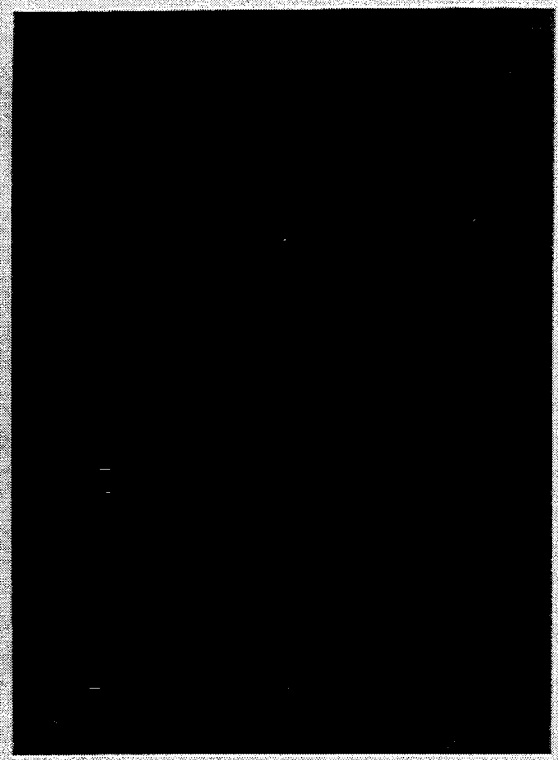
FIG. 1A  FIG. 1B
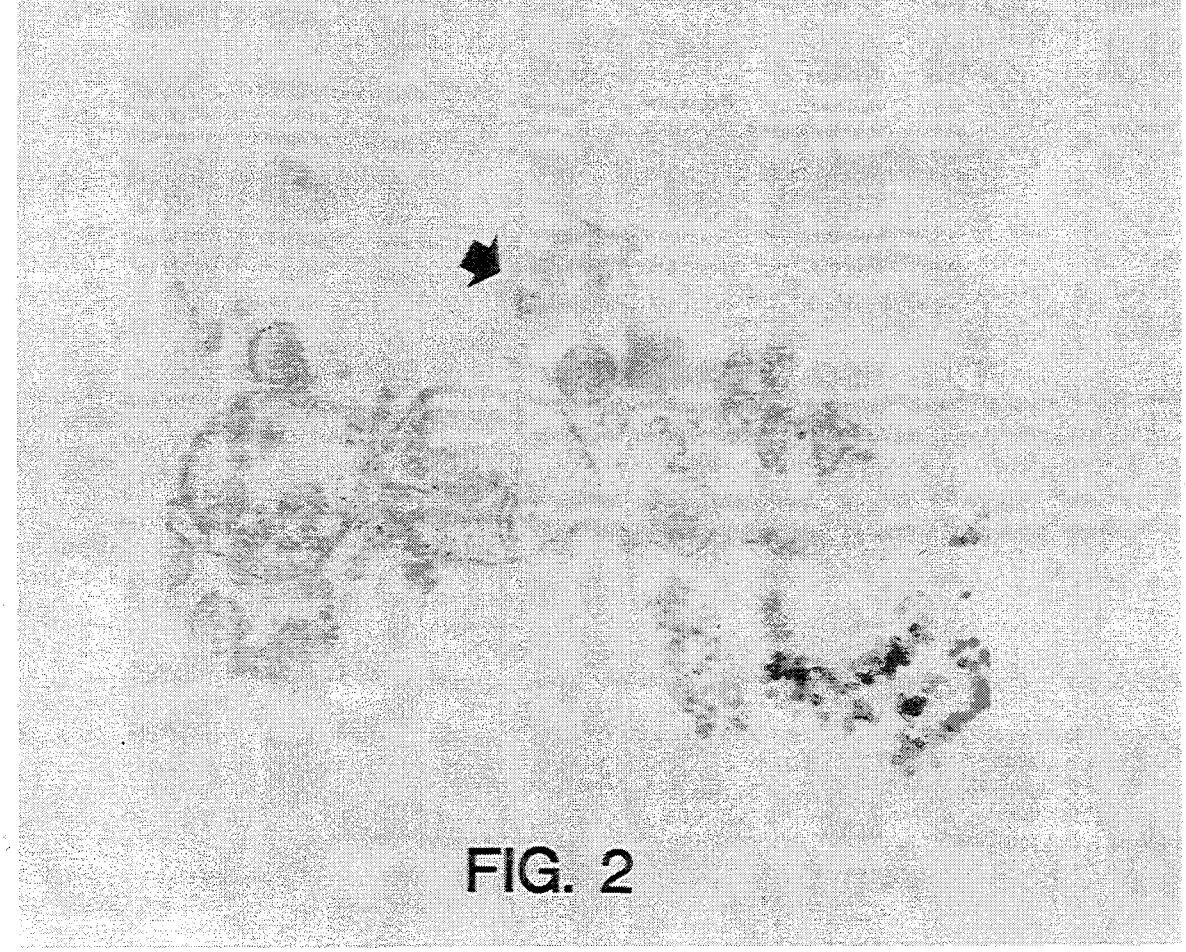
FIG. 2

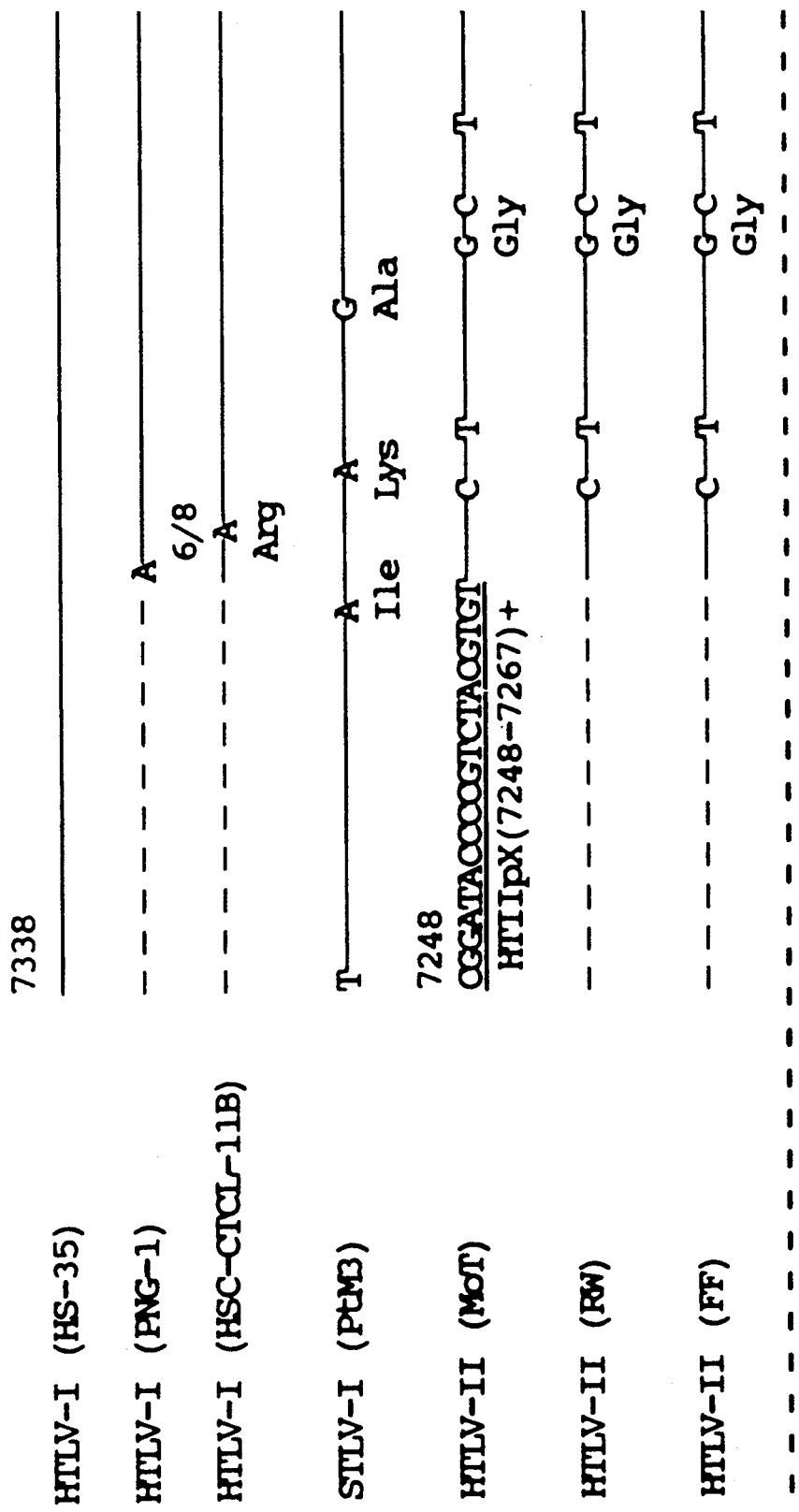

FIG. 3A-2

```
                                                                7438
HTLV-I (EMBL)    CCCCATCTCGGGGACTATGTTCGCCCGCCT
                 ProHisLeuTrpGlyThrMetPheGlyProPro
                                                                7418
HTLV-I (HS-35)   ─────────────────────────────

HTLV-I (PNG-1)   ─────────────────────────────

HTLV-I (HSC-CTCL-11B)  ─────────────────────────────

C                   7328
STLV-I (PtM3)    ───────────────────────────────
                                            Ser

HTLV-II (MoT)    ───T──G────A─T──T────────CA─
                    SerArg  ArgTrpSer     His

HTLV-II (RW)     ───T──G────A─T──T────────CA─
                    SerArg  ArgTrpSer     His

HTLV-II (FF)     ───T──G────A─T──T────────CA─ ─ ─
                    SerArg  ArgTrpSer     His
```

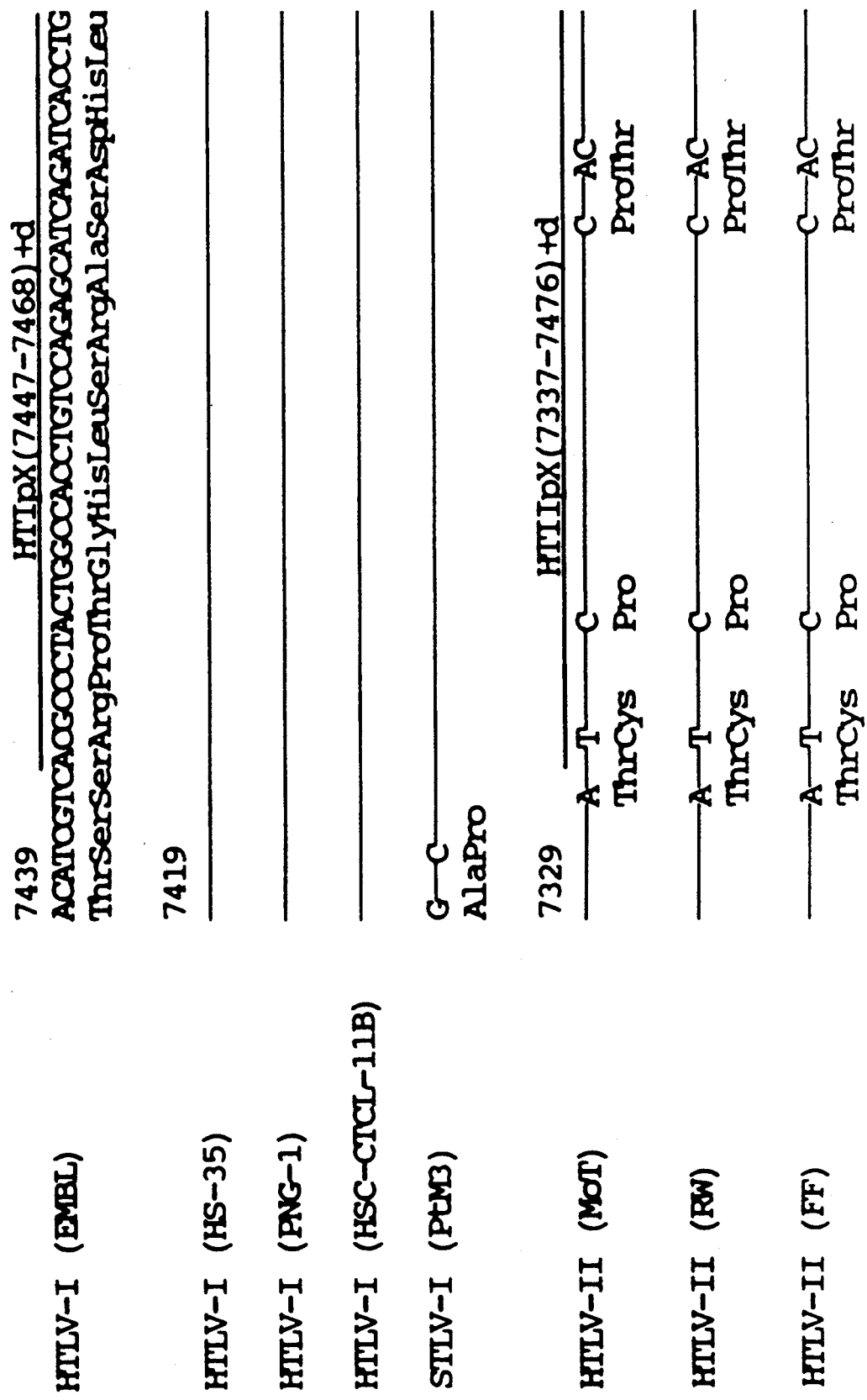

FIG. 3A-4

```
                                              7516
HTLV-I  (EMBL)       GGACCCATGGATGACGGTTATGGCTC   HTlpX(7516-7496)-
                     GlyProHis
                                              7496
HTLV-I  (HS-35)      ———————G——A———————————————  ——
HTLV-I  (PNG-1)      ——————————————————————————  ——
HTLV-I  (HSC-CTCL-11B) ————————————————————————  ——
STLV-I  (PtM3)       ——————————C——A————————————  ——
                                              7406
HTLV-II (MoT)        CGATGGACGGTTGTCAGCTC         HTlIpX(7406-7386)-
HTLV-II (RW)         ——————————————————————————  ——
HTLV-II (FF)         ——————————————————————————  ——
```

FIG. 3B-1

B (pol)

```
             4757
HTLV-I (EMBL)    CCCTACAATCAACCAGCTCAGGACTGTAGAAGCTCTAATGGCATT
                 HTIP(4757-4778)+   GlyLeuValGluArgSerAsnGlyIle

4737
HTLV-I (HS-35)   ─────────────────C──────────────────────────

HTLV-I (PNG-1)   ─────────────────────────────G──────────────

HTLV-I (HSC-CTCL-11B) ────────────────────G───────────────────

4735
HTLV-II (MoT)    CCCTACAATCAACCAGCTCAG─C─G─C─GA─AA─C────TG─A
                 HTIIP(4735-4756)+         Thr         Val

HTLV-II (RW)     ─────────────────────C─G─C─GA─AA─C────TG─A
                                           Thr         Val

HTLV-II (FF)     ─────────────────────C─G─C─GA─AA─C────TG─A
                                           Thr         Val
```

FIG. 3B-2

B (pol)

```
                              HTIP(4825-4850)+d    4852
HTLV-I (EMBL)     CTTAAAACCTATTATATAAGTACTTTACTGACAAACCGACCTACCC
                  LeuLysThrLeuLeuTyrLysTyrPheThrAspLysProAspLeuPro

4832
HTLV-I (HS-35)    ——————————————————————T————————————————————

HTLV-I (PNG-1)    ————TT————————————C—G—A—T—————————————————
                      Ile              HisArg Asn

HTLV-I (HSC-CTCL-11B) ——————————————————————————————————————

4830
HTLV-II (MoT)     A-C———A-T—C—A———A—T—ACTA—TGT—T/A—T——————
                  Ile    Asn    Asn    LeuLeu Cys Asn

HTLV-II (RW)      A-C———A-T—C—A———A—T—ACTA—TGT—T/A—T——————
                  Ile    Asn    Asn    LeuLeu Cys Asn

HTLV-II (FF)      A-C———A-T—C—A———A—T—ACTA—TGT—T/A—T——————
                  Ile    Asn    Asn    LeuLeu Cys Asn
```

FIG. 3B-3

```
                4853
HTLV-I  (EMBL)  ATGGATATAATGCTCTATCCTATGGACAATCAACCACTGAAT
                MetAspAsnAlaAlaSerIleAlaLeuTrpThrIleAsnHisLeuAsn

4833
HTLV-I  (HS-35) ─────────────────────────────A──────────────

HTLV-I  (PNG-1) ──────G──────T───────T──────────────────────
                   Glu

HTLV-I  (HSC-CTCL-11B) ─────────────────────────────────────

4831
HTLV-II (MoT)   ──C─A────C────CA─TCA──A──────────T───TC───G─
                   Leu        IleHisLys                LeuAsnGln

HTLV-II (RW)    ──C─A────C────CA─TCA──A──────────T───TC───G─
                   Leu        IleHisLys                LeuAsnGln

HTLV-II (FF)    ──C─A────C────CA─TCA──A──────────T───TC───G─
                   Leu        IleHisLys                LeuAsnGln
```

FIG. 3B-4

```
                                                        GTGTAACCAACTGCCACAAACCGATGGCAGCTTCACCAC  4942
HTLV-I  (EMBL)                                          ValLeuThrAsnCysHis    HTIP(4942-4919)
                                                                                              4922
HTLV-I  (HS-35)                         ————————A——————————————————————————————————

HTLV-I  (PNG-1)                         ————————————T—————————————————————————————

HTLV-I  (HSC-CTCL-11B)                  ——————————————————————————————————————————

4920
                                        HTIIP(4880-4898)+d                    GGCAGCTTCACCAC
HTLV-II (MoT)                           ————CA————A-TGGTAAACCGATGGCAGCTTCACCAC  HTIIP(4920-4897)
                                                  MetAsnProSerGly

HTLV-II (RW)                            ————CA————A-TGGT—————————————————————
                                                  MetAsnProSerGly

HTLV-II (FF)                            ————CA————A-TGGT—————————————————————
                                                  MetAsnProSerGly
```

```
HTLV-I (EMBL)
6293                                              HTLE(6330-6368)+d
CCACAAAATCTACTCAAATTGCGCAGTATGCTGCCCAGAACAGAGAGGCCTTGATCTCCTGTTCTGG
           HTLE(6293-6324)+        AlaAlaGlnAsnArgArgGlyLeuAspLeuLeuPheTrp

HTLV-I (HS-35)
6273                ─────────G──────────A─────────────────────────────────

HTLV-I (PNG-1)
        ─ ─ ─ ─ ─ ─ ─ ─ ─ ─ ─ ─ ─ ─ ─ ─ ─ ─ ─ ─ ─ ─ ─ ─ ─ ─ ─ ─ ─ ─

HTLV-I (HSC-CTCL-11B)
        ─ ─ ─ ─ ─ ─ ─ ─ ─ ─ ─ ─ ─ ─ ─ ─ ─ ─ ─ ─ ─ ─ ─ ─ ─ ─ ─ ─ ─ ─

STLV-I (PtM3)
                         ──G────A───A──────────A──────A───────T─────────

HTLV-II (MoT)
6258
T──TC────CA-C────CGGG────A───A────A────A────AT-A─-C───A────────────

```
                    GAGCAAGGAGGATTATGCAAGCATTACAGAAGAACAGTGCCGTTTCG    6410
HTLV-I (EMBL)       GluGlnGlyGlyLeuCysLysLysAlaLeuGlnGluGlnCysArgPhePro
6293

HTLV-I (HS-35)      ─────────────────────────T──────────────────TA     6390
6273                                         Cys                Leu

1/6
HTLV-I (PNG-1)      ──A────────G──GC────G───T───────────────────TA
                                        Arg  Cys                Leu

HTLV-I (HSC-CTCL-11B) ─────────────────────T──────────────────────TA
                                          Cys                     Leu

STLV-I (PtM3)       ──────────────────C──G──TT──────────────────C-TA
                                              Cys                 Leu

HTLV-II (MoT)       ──A────G──T──G────G──CA──G──A──TT-C──C──TC   6376
6258                        Ile                    Cys        Leu
                    ─ ─ ─ ─ ─ ─ ─ ─ ─ ─ ─ ─ ─ ─ ─ ─ ─ ─ ─ ─ ─ ─
```

FIG. 3C-3

```
HTLV-I (EMBL)
6411
AATATTACCAATCCATGTCCAATACTACAAGAAACCCCCTTGAGAATGAGTCTGACTGCC
AsnIleThrAsnSerHisValProIleLeuGlnGluArgProLeuGluAsnArgValLeuThrGly

HTLV-I (HS-35)                  T           G        A
6391                           Ser

HTLV-I (PNG-1)         CC   TT  T           A
                       Pro  Ser

HTLV-I (HSC-CTCL-11B)           T
                               Ser

STLV-I (PtM3)                   T           A        T
                               Ser

HTLV-II (MoT)    C  GT  CA T    AT CG C C C  CC G T  A A T  A C C
6377             Ser  Thr       SerVal                Lys    Ile
```

FIG. 3C-4

```
HTLV-I    TGGGGCTTAACTGGGACTTGGCCTCTCACAGTGGCTGGAGAGGCC  6527
(EMBL)    TrpGlyLeuAsnTrpAsp       HTIE(6527-6498)—
6411

HTLV-I    ————————————A———————————————————————————————  6507
(HS-35)
6391

HTLV-I    ————————T—*—————————————————————————————————
(PNG-1)           ThrGlyThr

HTLV-I    ————————————————————————————————————————————
(HSC-CTCL-11B)

STLV-I    ————C———————————————————G——A———————————C————
(PtM3)

HTLV-II   ——A————A————T———————————A———G———C———————A——A  6492
(MoT)
6377
```

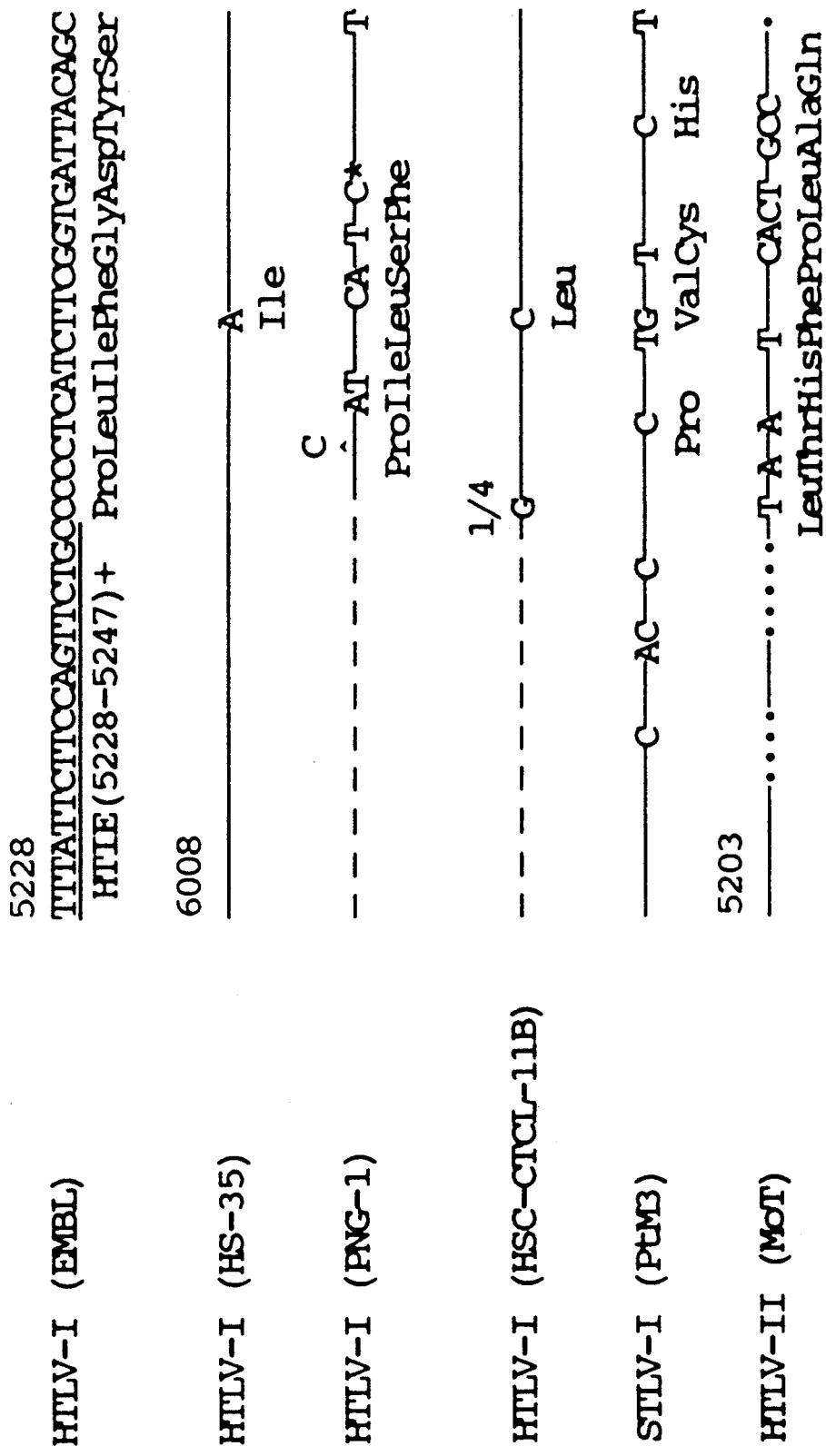

HTLV-I (EMBL)

```
                                                        5321
         HTLE(5271-5305)+d
CCCAGCTGTACTCTCACAATGGAGTCTCCTCATACCACTCTAAACC
ProSerCysThrLeuThrIleGlyValSerSerTyrHisSerLysPro
                        5301
```

HTLV-I (HS-35) ────────────G──────────────────
                            Val

HTLV-I (PNG-1) ──────────────────T────────────

1/4
HTLV-I (HSC-CTCL-11B) ────C─────────────G──────
                          Arg              Glu

STLV-I (PtM3) ──────────C──────G-C────T────────
                                Val

5287
HTLV-II (MoT) ──AG──C-A──C-A──G──TA──C──C-GC─
               Gln  Arg      Ile    Ser

FIG. 3D-3

```
                5322
                TGCAATCCTGCCCAGCCAGTTGTGTGACCTGGAC
                CysAsnProAlaGlnProValCysSerTrpThrLeuAsp
                5302
HTLV-I (EMBL)   ────────────────────────────────
HTLV-I (HS-35)  ──────────────A───────────────── 1/5
HTLV-I (PNG-1)  ─────────C───A──────────────T───
HTLV-I (HSC-CTCL-11B) ─────────────────────────
STLV-I (PtM3)   ──────C──A────C──C──A───────────
                5288
HTLV-II (MoT)   ──T-GC──AA──A──C──C──CA────A────
                  Ser Thr                Thr Asn
```

FIG. 3D-4

```
                                                            5414
CTGCTGGCCTTCAGCAGATCAGGCCTACAGCCCCTCCTAACCTAGTA
LeuLeuAlaAlaLeuSerAlaAspGlnAlaLeuGlnProProCysProAsnLeuVal
                                    5394
HTLV-I (EMBL)

HTLV-I (HS-35)     ────────────────A───────T─────────

1/5
HTLV-I (PNG-1)     ─T──────────────────────GT─────────G
                                            Ser

HTLV-I (HSC-CTCL-11B) ─────────────────────T──────────

5380
STLV-I (PtM3)      ──A─T──C──C─A────────T──G──────G
                              Thr

HTLV-II (MoT)      ──TAATT──AA─A─G──C──ACGA──────A─T
                     AsnSer   ThrThr   Arg His      Ile
```

```
                    5415
HTLV-I (EMBL)       AGTTACTCCAGCTACCATGCCACCTATTCCTATATCTA
                    SerTyrSerSerTyrHisAlaThrTyrSerLeuTyrLeu

5395
HTLV-I (HS-35)      ————————————————————————————————————

HTLV-I (PNG-1)      ———————————C——————————————————————
                               Asn

HTLV-I (HSC-CTCL-11B) G————————T-A——————————————————————
                      Gly       Asn

STLV-I (PtM3)       G——————————A———————————T——————————
                    Gly         Asn

5381
HTLV-II (MoT)       ——C——TG——T——AAG——T——————T——————CT
                      Thr SerGlyPhe Lys
```

```
                                                                      5504
HTLV-I (EMBL)         TTCCCTCATTGGACTAAGAAGCCAAACCGAAATGGCGAGGCTATTATTCA
                      PheProHisTrpThrLysLysProAsnArgAsnGlyGlyTyrTyrTyrSer
                                        5484
HTLV-I (HS-35)        ─────────TC──A──────────────────────────
                                  Ile
HTLV-I (PNG-1)        ──────────T──A──────────C─────────G──────
                                  Ile
HTLV-I (HSC-CTCL-11B) ──────────T──A──────────────────────────
                                  Ile
STLV-I (PtM3)         ──────────T──A──────────────────G──────
                                  Ile                                  5470
HTLV-II (MoT)         ──A───────TA──A──────A──C─G──CT──G──C─C─G
                                  Ile       Gln    Leu
```

FIG. 3E-3

```
                    5505
HTLV-I (EMBL)       GCCTCTTATTCAGACCCTTGTTCTTAAAGTGCCCATAC
                    AlaSerTyrSerAspProCysSerLeuLysCysProTyr

5485
HTLV-I (HS-35)      ————————————A—————————————————————————

HTLV-I (PNG-1)      ——————————————————————————————————————

HTLV-I (HSC-CTCL-11B) ————————————————————————————————————

STLV-I (PtM3)       ——————————————————T———————————————————

5471
HTLV-II (MoT)       C-T———C—CAAT————————C—GC—C————————————
                    Pro     Asn         Gln
```

```
                 6046
HTLV-I_ATK      TCATAACTCC CTCATCCTGC CCCCCT
HTLV-I_mel 1    ─────────────────────────T─
HTLV-I_mel 2    ─────────────────────────T─
HTLV-I_mel 3    ───────────────────────────
HTLV-I_mel 4    ───────────────────────────
HTLV-I_mel 5    ───────────────────────────
HTLV-I_mel 6    ───────────────────────────
HTLV-I_bel 1    ───────────────────────────
HTLV-I_bel 2    ───────────────────────────

HTLV-I_ATK      TTTC CTTGTCACCT GTTCCACCC TA
HTLV-I_mel 1    ─────C──────────────G────T──
HTLV-I_mel 2    ─────C──────────────G────T──
HTLV-I_mel 3    ─────C───────C──────GG──────
HTLV-I_mel 4    ─────C───────C──────GG──────
HTLV-I_mel 5    ─────C───────C──────GG────C─
HTLV-I_mel 6    ─────C───────C──────GG──────
HTLV-I_bel 1    ─────────────C──────────────
HTLV-I_bel 2    ─────────────C────────────── gp46 ← │ → gp21
                               ↓
HTLV-I_ATK      GGATCCCG CTCCCGCCGA GCGGTACC
HTLV-I_mel 1    CA───────T──────────────────
HTLV-I_mel 2    CA───────T──────────────────
HTLV-I_mel 3    C────────T──────────G───────
HTLV-I_mel 4    C────────T──────────────────
HTLV-I_mel 5    C────────T───────────────G──
HTLV-I_mel 6    C────────T──────────────────
HTLV-I_bel 1    ────────────────────────────
HTLV-I_bel 2    ────────────────────────────

HTLV-I_ATK      GG TGGCGGTCTG GCTTGTCTCC GCC
HTLV-I_mel 1    A─────────────────A─────────
HTLV-I_mel 2    A─────────────────A─────────
HTLV-I_mel 3    ──────────────────A─────────
HTLV-I_mel 4    ──────────────────A─────────
HTLV-I_mel 5    ──────────────────A─────────
HTLV-I_mel 6    ──────────────────A─────────
HTLV-I_bel 1    ────────────────────────────
HTLV-I_bel 2    ───C────T───────────────────
```

FIG. 4A

```
HTLV-I_ATK   CTGGCCA TGGGAGCCGGAGTGGCTGGC
HTLV-I_mel1  ———————————A———A————A-T———
HTLV-I_mel2  ———————————G———A————A-T———
HTLV-I_mel3  ———————————————A———GA-T———
HTLV-I_mel4  ———————————————A———GA-T———
HTLV-I_mel5  ———————————————A———GA-T———
HTLV-I_mel6  ———————————————A———GA-T———
HTLV-I_bel1  ———————————————————G——————
HTLV-I_bel2  ———————————————————G——————

HTLV-I_ATK   GGGATTACCG GCTCCATGTC CCTCGC
HTLV-I_mel1  ——————T———————————————————
HTLV-I_mel2  ——————T———————————————————
HTLV-I_mel3  -A————————————————————————
HTLV-I_mel4  ——————————————————————————
HTLV-I_mel5  -A————————————————————————
HTLV-I_mel6  ——————————————————————————
HTLV-I_bel1  ——————————————————————————
HTLV-I_bel2  ——————————————————————————

HTLV-I_ATK   CTCA GGAAAGAGCCTCCTACATGA GG
HTLV-I_mel1  ———————————T———————————————
HTLV-I_mel2  ———————————T———————————————
HTLV-I_mel3  ———————————T———————————————
HTLV-I_mel4  ——T————————T———————————————
HTLV-I_mel5  ———————————T———————————————
HTLV-I_mel6  ——T————————T———————————————
HTLV-I_bel1  ————————————————————T——————
HTLV-I_bel2  ————————————————————T——————

HTLV-I_ATK   TGGACAAA GATATTTCCC AGTTAACT
HTLV-I_mel1  -A——————G———————————A———————
HTLV-I_mel2  -A——————G———————————A———————
HTLV-I_mel3  -A——————————————————A———C———
HTLV-I_mel4  -A——————————————————A———C———
HTLV-I_mel5  -A——————————————————A———C———
HTLV-I_mel6  -A——————————————————A———C———
HTLV-I_bel1  ————————————————————A———————
HTLV-I_bel2  ————————————————————A———————
```

FIG. 4B

```
HTLV-I_ATK    CA AGCAATAGTC AAAAACCACA AAAA
HTLV-I_mel 1  ———————————————T—————————————
HTLV-I_mel 2  ———————————————T—————————————
HTLV-I_mel 3  ———————————————T—————————————
HTLV-I_mel 4  ———————————————T—————————————
HTLV-I_mel 5  ———————————————T—————————————
HTLV-I_mel 6  ———————————————T—————————————
HTLV-I_bel 1  —————————————————————————————
HTLV-I_bel 2  —————————————————————————————

HTLV-I_ATK    TCTACTCAAAATTGCG CAGTATGCTG
HTLV-I_mel 1  ————————G———————A———A—————
HTLV-I_mel 2  ————————G———————A———A—————
HTLV-I_mel 3  ————————————————A———A—————
HTLV-I_mel 4  ————————————————A———A—————
HTLV-I_mel 5  ————————————————A———A—————
HTLV-I_mel 6  ————————————————A———A—————
HTLV-I_bel 1  ——————————————————————————
HTLV-I_bel 2  ——————————————————————————

HTLV-I_ATK    CCCAGAACAG ACGAGGCCTT GATCTCC
HTLV-I_mel 1  ———————————————————————————————
HTLV-I_mel 2  ———————————————————————————————
HTLV-I_mel 3  ———————————————————————————————
HTLV-I_mel 4  ———————————————————————————————
HTLV-I_mel 5  ————————————————————C——————————
HTLV-I_mel 6  ———————————————————————————————
HTLV-I_bel 1  ———————————————————————————————
HTLV-I_bel 2  ———————————————————————————————

HTLV-I_ATK    TGTTCTGGGAGCA AGGAGGATTA TGCA
HTLV-I_mel 1  ——————————A—————————————————————
HTLV-I_mel 2  ——————————A—————————————————————
HTLV-I_mel 3  ——————————A—————————————————————
HTLV-I_mel 4  ——————————A—————————————————————
HTLV-I_mel 5  ——————————A—————————————————————
HTLV-I_mel 6  ——————————A—————————————————————
HTLV-I_bel 1  ————————————————————————————————
HTLV-I_bel 2  ————————————————————————————————
```

FIG. 4C

```
HTLV-I_ATK   AAGCAT  TACAAGAACA  GTGCCGTTTT
HTLV-I_mel1  -G--GC----------------T-----
HTLV-I_mel2  -G--GC----------------T-----
HTLV-I_mel3  -G--GC----------------T-----
HTLV-I_mel4  -G--GC----------------T-----
HTLV-I_mel5  -G--GC----------------T-----
HTLV-I_mel6  -G--GC----------------T-----
HTLV-I_bel1  ----------------------T-----
HTLV-I_bel2  ----------------------T-----

HTLV-I_ATK   CCGAATATTA  CCAATTCCCA TGTCCCAA
HTLV-I_mel1  -TA--C--C------T-------C--TT----
HTLV-I_mel2  -TA--C--C------T-------C--TT----
HTLV-I_mel3  -TA--C---------T-------C--TT-C--
HTLV-I_mel4  -TA--C---------T-------C--TT-C--
HTLV-I_mel5  -TA--C---------T-------C--TT-C--
HTLV-I_mel6  -TA--C---------T-------C--TT-C--
HTLV-I_bel1  -TA------------T----------T-----
HTLV-I_bel2  -TA------------T----------T-----

HTLV-I_ATK   TA CTACAAGAAA  GACCCCCCT  TGAG
HTLV-I_mel1  ---------------------A---------
HTLV-I_mel2  ---------------------A---------
HTLV-I_mel3  ---------------------A---------
HTLV-I_mel4  ---------------------A---------
HTLV-I_mel5  ---------------------A---------
HTLV-I_mel6  ---------------------A---------
HTLV-I_bel1  -----------------------------G-
HTLV-I_bel2  -----------------------------G-

HTLV-I_ATK   AATCGA  GTCCTGACTGGCTGGGGCCT TA
HTLV-I_mel1  --------------------------T-----
HTLV-I_mel2  --------------------------T-----
HTLV-I_mel3  --------------------------T-----
HTLV-I_mel4  --------------------------T-----
HTLV-I_mel5  --------------------------T-----
HTLV-I_mel6  --------------------------T-----
HTLV-I_bel1  --------------------------------
HTLV-I_bel2  --------------------------------
```

FIG. 4D

```
HTLV-I_ATK   ACTGGGAC CTTGGCCTCT CACAGTGGG
HTLV-I_mel1  ———————————————————————A————
HTLV-I_mel2  ———————————————————————A————
HTLV-I_mel3  ———————————————————————A————
HTLV-I_mel4  ———————————————————————A————
HTLV-I_mel5  ———————————————————————A————
HTLV-I_mel6  ———————————————————————A————
HTLV-I_bel1  ————————————————————————————
HTLV-I_bel2  ——————————————————C—————————

HTLV-I_ATK   C TCGAGAGGCC TTACAAACTG GAATC
HTLV-I_mel1  —C——————————C—G—————————C——
HTLV-I_mel2  —C——————————C—G—————————C——
HTLV-I_mel3  —C——————————C———————————C——
HTLV-I_mel4  —C——————————C———————————C——
HTLV-I_mel5  —C——————————C———————————C——
HTLV-I_mel6  —C——————————C———————————C——
HTLV-I_bel1  ————————————————————————————
HTLV-I_bel2  ———G————————————————————————

HTLV-I_ATK   ACCCTTGTTGCGCTA CTCCTTCTTGTTA
HTLV-I_mel1  ——————A————————————————————
HTLV-I_mel2  ——————A————————————————————
HTLV-I_mel3  ———————————————————————————C—
HTLV-I_mel4  ———————————————————————————C—
HTLV-I_mel5  —————————————————————————————
HTLV-I_mel6  ———————————————————————————C—
HTLV-I_bel1  ————C————————G———————————————
HTLV-I_bel2  ————C————————G———————————————

6567
HTLV-I_ATK   TCCTTGC AGGACCATGC  AT
HTLV-I_mel1  ——————————————————
HTLV-I_mel2  ——————————————————
HTLV-I_mel3  ——————————————————
HTLV-I_mel4  ——————————————————
HTLV-I_mel5  ——————————————————
HTLV-I_mel6  ——————————————————
HTLV-I_bel1  ——————————————————
HTLV-I_bel2  ——————————————————
```

```
                                 GP46 ←―|―→ GP21
                                        ↓
HTLVI_MT2     H N S L I L P P F S L S P V P T L G S R S R R A V P V A
Melanesia 1                                       Q
Melanesia 2                                       Q
Melanesia 3                           A           R
Melanesia 4                           A           R
Melanesia 5                           A P R
Melanesia 6                           A           R
Bellona 1
Bellona 2                                                     A V
STLVI_MAC                           A P
HTLVII        P P A T               R             -

V W L V S A L A M G A G V A G G I T G S M S L A S G K S L L H
Melanesia 1           -       T     - - - -
Melanesia 2                   T     - - - -
Melanesia 3                   T     - - - -                         R
Melanesia 4                   T     - - - -
Melanesia 5                   T     - - - -                         R
Melanesia 6                   T     - - - -
Bellona 1
Bellona 2
STLVI_MAC             A       T   I   V   L           S               L
HTLVII                A       T   I   V   L           S               L
```

FIG. 5B

|  | E V D K D I S Q L T Q A I V K N H K N L L K I A Q Y A A Q N |
|---|---|
| HTLVI<sub>MT2</sub> | |
| Melanesia 1 | |
| Melanesia 2 | V |
| Melanesia 3 | V |
| Melanesia 4 | |
| Melanesia 5 | |
| Melanesia 6 | |
| Bellona 1 | |
| Bellona 2 | |
| STLVI<sub>MAC</sub> | |
| HTLVII | |

|  | R R G L D L L F W E Q G G L C K A L Q E Q C C F L N I T N |
|---|---|
| HTLVI<sub>MT2</sub> | |
| Melanesia 1 |         H                 Q   I   R V |
| Melanesia 2 | |
| Melanesia 3 | |
| Melanesia 4 | |
| Melanesia 5 | R |
| Melanesia 6 | |
| Bellona 1 | |
| Bellona 2 | |
| STLVI<sub>MAC</sub> |                                  I |
| HTLVII |                                                S |

FIG. 5C

|  | | | | | | | | | | | | | | | | | | | | | | | |
|---|---|---|---|---|---|---|---|---|---|---|---|---|---|---|---|---|---|---|---|---|---|---|---|
| HTLVI_MT2   | S | H | V | S | I | L | Q | E | R | P | P | L | E | N | R | V | L | T | G | W | G | L | N | W | D | L | G | L | S |
| Melanesia 1 | | | | | | | | | | | | | | | | | | | | | | | | | | | | | |
| Melanesia 2 | | | | | | | | | | | | | | | | | | | | | | | | | | | | | |
| Melanesia 3 | | | | | | | | | | | | | | | | | | | | | | | | | | | | | |
| Melanesia 4 | | | | | | | | | | | | | | | | | | | | | | | | | | | | | |
| Melanesia 5 | | | | | | | | | | | | | | | | | | | | | | | | | | | | | |
| Melanesia 6 | | | | | | | | | | | | | | | | | | | | | | | | | | | | | |
| Bellona 1   | | | | | | | | | | | | | | | | | | | | | | | | | | | | | |
| Bellona 2   | | | | | | | | | | | | | | | | | | | | | | | | | | | | | |
| STLVI_MAC   | | | | | | | | | | | | | | | | | | | | | | | | | | | | | |
| HTLVII      | | | | | | | | | | | | | | | | | | | | | | P | | | | | | | |

|  | | | | | | | | | | | | | | | | | | | | | | | |
|---|---|---|---|---|---|---|---|---|---|---|---|---|---|---|---|---|---|---|---|---|---|---|---|
| HTLVI_MT2   | Q | W | A | R | E | A | L | Q | T | G | I | T | L | V | A | L | L | L | V | I | L | A | G | P | C |
| Melanesia 1 | | | | | | | | | | | | | | | | | | | | | | | | | |
| Melanesia 2 | | | | | | | | | | | | | | | | | | | | | | | | | |
| Melanesia 3 | | | | | | | | | | | | | | | | | | | | | | | | | |
| Melanesia 4 | | | | | | | | | | | | | | | | | | | | | | | | | |
| Melanesia 5 | | | | | | | | | | | | | | | | | | | | | | | | | |
| Melanesia 6 | | | | | | | | | | | | | | | | | | | | | | | | | |
| Bellona 1   | | | | | | | | | | G | | | | | | | | | | | | | | | |
| Bellona 2   | | | | | | | | | | | | | | | | | | | | | | | | | |
| STLVI_MAC   | T | | | | | V | | | K | | I | | | | | | | | | | L | | | | |
| HTLVII      | | | | | | | | | | | | | | V/F | | | | | | | | | | | I |

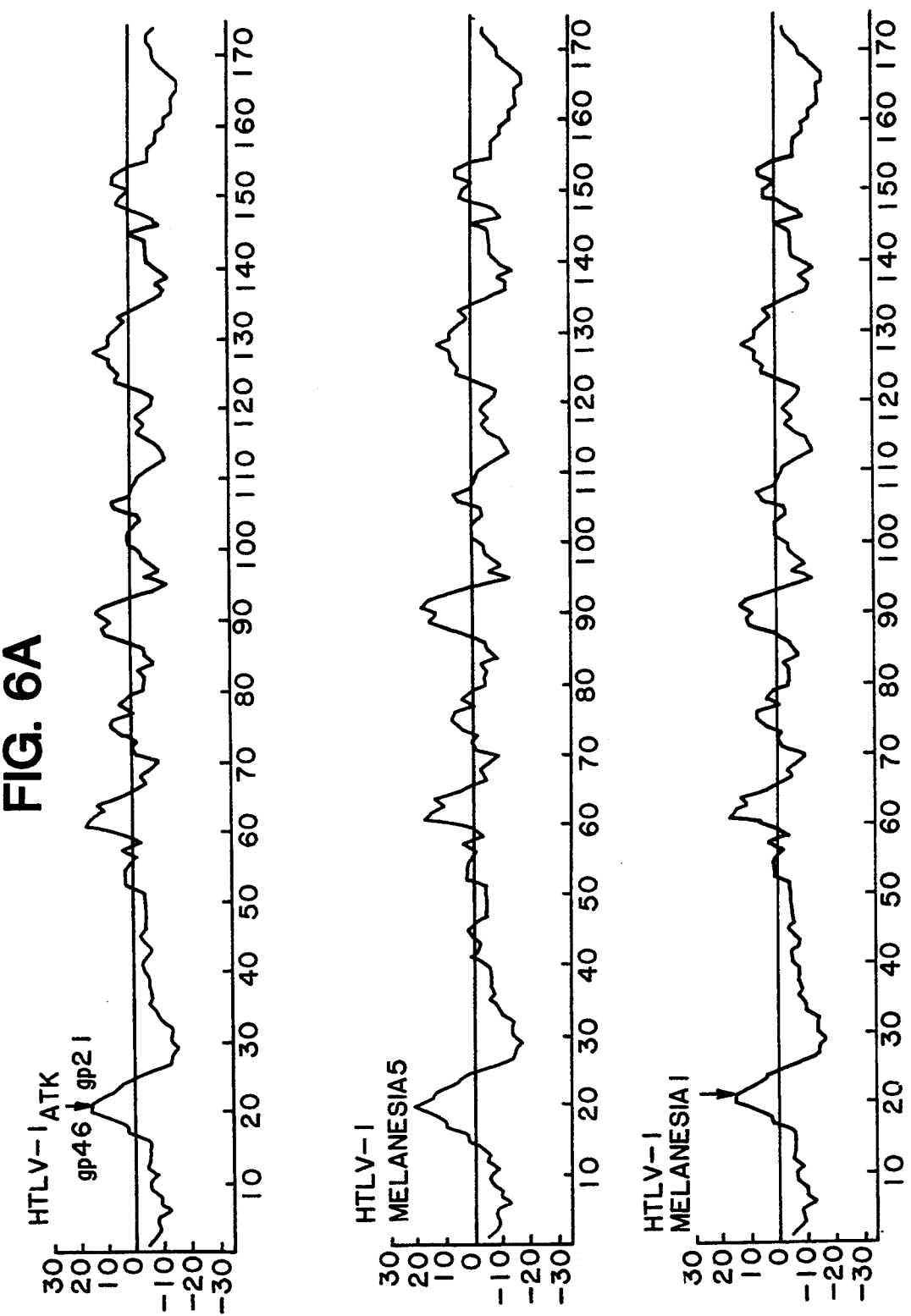

PAPUA NEW GUINEA HUMAN T-LYMPHOTROPIC VIRUS

This is a continuation-in-part application of Yanagihara et al. Ser. No. 07/572,090, filed Aug. 24, 1990, now abandoned, the entire contents of which are hereby incorporated by reference.

BACKGROUND OF THE INVENTION

1. Field of the Invention

The present invention relates to Papua New Guinea variants of HTLV-I. In particular, the present invention relates to a human T-cell line persistently infected with a Papua New Guinea HTLV-I variant. The present invention further relates to bioassays and kits for the diagnosis of HTLV-I infections.

BACKGROUND INFORMATION

The human T-cell leukemia lymphoma viruses (HTLV) represent a group of type C, exogenous and replication-competent retroviruses linked antigenically and by sequence homology (Retrovirus Biology and Human Disease. Eds. Gallo and Wong-Staal, Marcel Dekker Inc., NY 1989). HTLV-I, a member of this group, is the causative agent of adult T-cell leukemia/-lymphoma (Poeisz et al., PNAS USA 1980; 77:7415-7419 and Hinuma et al., PNAS USA 1981; 78:6476-6480) and tropical spastic paraparesis/HTLV-I-associated myelopathy (Gessain et al., Lancet 1985; 2:407-410; Rodgers-Johnson et al., Lancet 1985; 2:1247-1248; and Osame et al., Lancet 1986; 1:1031-1032) Due to the genetic variability between HTLV-I isolates from Melanesia and other geographical locales, the widespread screening for infection in human populations in Melanesia can be best served by using a virus strain which is indigenous to that area.

High prevalences of antibodies against HTLV-I have been reported for several coastal and inland Melanesian populations, by using screening tests such as enzyme immunoassay and gelatin particle agglutination (Kazura et al., J. Infect. Dis. 1987; 155:1100-1107; Asher et al., J. Med. Virol. 1988; 26:339-351; Brindle et al., Epidemiol. Infect. 1988; 100:153-156; Brabin et al., Int. J. Cancer 1989; 44:59-62; Re et al., AIDS Res. Hum. Retroviruses 1989; 5:551-554; Armstrong et al., Am. J. Phys. Anthropol. 1990; 81:465-470; Garruto et al., Am. J. Hum. Biol. 1990; 2:439-447; and Imai et al., Jpn. J. Cancer Res. 1990; 81:1218-1221). These reported high prevalences of antibodies against HTLV-I, however, have been viewed with skepticism by some investigators because of the failure of such Melanesian sera to neutralize a prototype strain of HTLV-I (Weber et al., J. Infect. Dis. 1989; 159:1025-1028). The present inventors, however, have demonstrated an HTLV-I seroprevalence of 14% among the Hagahai (Yanagihara et al., J. Infect. Dis. 1990; 162:649-654), a remote, recently contacted hunter-horticulturalist group living in the highland fringe of Papua New Guinea (Jenkins, Soc. Sci. Med. 1988; 26:997-1006), and seroprevalences of 2% to 10% among inhabitants from widely separated regions in the Solomon Islands (Yanagihara et al., Am. J. Trop. Med. Hyg. 1991; 44:122-130). The serological data are consistent with the existence of variant viruses, phylogenetically related to but distinct from cosmopolitan prototype HTLV-I (Asher et al., J. Med. Virol. 1988; 26:339-351; Garruto et al., Am. J. Hum. Biol. 1990; 2:439-447; Yanagihara et al., J. Infect. Dis. 1990; 162:649-654; and Yanagihara et al., Am. J. Trop. Hyg. 1991; 44:122-130). The present inventors have also established the existence of HTLV-I in Melanesia with the isolation of HTLV-I-like viruses from a healthy Hagahi man (Yanagihara et al., N. Engl. J. Med. 1990; 323:993-994; and Yanagihara et al., PNAS USA 1991; 88:1146-1150) and from unrelated Solomon Islanders (Yanagihara et al., Jpn. J. Cancer Res. 1991; 44:240-244).

The establishment of a cell line persistently infected with an HTLV-I variant, derived from a healthy New Guinean, would facilitate testing in Melanesia, where high prevalences of HTLV-I infection have been found. Such a cell line would also have important application in testing populations elsewhere in the world and in the development of a vaccine for the prevention of infection with and of diseases caused by HTLV-I and related viruses. In addition, methods and diagnostic kits which detect Melanesian HTLV-I variants may obviate serodiagnostic problems encountered in Melanesia and in other geographical regions where serological tests employing cosmoplitan prototypes of HTLV-I yield high frequencies of indeterminate results.

SUMMARY OF THE INVENTION

Accordingly, it is an object of the present invention to provide a human T-cell infected with an HTLV-I variant and the bioassays and diagnostic kits this variant affords.

It is another object of the present invention to provide a cell line persistently infected with a Papua New Guinean HTLV-I-related virus.

Various other objects and advantages of the present invention will become apparent from the figures and the following description of the invention.

In one embodiment, the present invention relates to a cell line, designated Papua New Guinea-1 (PNG-1) comprising an HTLV-I variant, for example, (ATCC CRL10528).

In another embodiment, the present invention relates to a purified antibody specific for a PNG-1 viral protein.

In a further embodiment, the present invention relates to a vaccine for humans against infection with and diseases caused by HTLV-I and related viruses comprising a non-infectious antigenic portion of the PNG-1 variant, in an amount sufficient to induce immunity against said infection and disease, and a pharmaceutically acceptable carrier.

In another embodiment, the present invention relates to bioassays for the diagnosis of infection with the PNG-1 variant. In one such bioassay PNG-1 cells are fixed on a solid support. The cells are then contacted with a biological sample from a human suspected of being infected and the presence or absence of a complex formed between proteins of cell and antibodies specific therefor present in said sample is detected.

In another bioassay a solid support is coated with viral protein and contacted with a biological sample from a human suspected of being infected, under conditions such that a complex is formed between the protein and antibodies specific therefor present in the sample. The presence or absence of the complex is then detected.

A further bioassay to which the present invention relates involves preparing a lysate from PNG-1 cells and contacting the lysate with a biological sample from a human suspected of being infected, under conditions such that a complex is formed between protein of the lysate and antibodies specific therefor present in the sample. The presence or absence of the formed complex is then detected.

The present invention also relates to bioassays for the diagnosis of infection with the PNG-1 variant by the detection of PNG-1 specific genomic sequences. The presence or absence of PNG-1 sequences can be detected by amplifying RNA in a biological sample using reverse transcriptase-directed polymerase chain reaction.

The present invention also relates to bioassays utilizing antibodies specific for PNG-1 viral proteins. In one bioassay, a solid support is coated with such antibodies and then contacted with a biological sample from a human suspected of having the infection under conditions such that the antibody forms a complex with PNG-1 viral proteins within the sample. The presence or absence of the complex is then detected.

In another embodiment, the present invention relates to a diagnostic kit comprising variant-specific peptides for the Papua New Guinea HTLV-I variant and ancillary reagents suitable for use in detecting the presence or absence of antibody-peptide complexes.

In a further embodiment, the present invention relates to a diagnostic kit comprising variant-specific oligonucleotide primers for the Papua New Guinea HTLV-I variant and ancillary reagents suitable for use in DNA amplification and detection.

BRIEF DESCRIPTION OF THE DRAWINGS

FIGS. 1A to 1B show virus-specific fluorescence in PNG-1 cells by double-label immunofluorescence test, using sera from (FIG. 1A) a Colombian patient with serologically confirmed HTLV-I myeloneuropathy and (FIG. 1B) a rabbit experimentally infected with HTLV-I, and antibodies to the respective IgG conjugated with fluorescein isothiocyanate (green) and rhodamine (red). Similar staining was observed using sera from HTLV-I-seropositive Hagahai, a Solomon Islander with HTLV-I myeloneuropathy and a rabbit antiserum prepared against the C-terminus of the major envelope glycoprotein gp46 of HTLV-I. No staining was observed with sera from HTLV-I-seronegative humans and rabbits, or monoclonal antibodies against HTLV-I gag-encoded proteins p19 and p24. (Original magnification, ×500)

FIG. 2 show a thin-section electron micrograph of PNG-1 cells demonstrating a solitary mature virus particle resembling HTLV-I (arrow). (Original magnification, ×90,000)

FIGS. 3A-1 to 3A-4, 3B-1 to 3B-4, 3C-1 to 3C-4, 3D-1 to 3D-4 and 3E-1 to 3E-4 show the sequence analysis of amplified, cloned DNA. DNA from virus infected cell lines was amplified and (FIGS. 3A-1 to 3A-4) pX, (SEQ ID NO:12 and SEQ ID NO:18), FIGS. 3B-1 to 3B-4 (SEQ ID NO:19 AND SEQ ID NO:20) pol, (FIGS. 3C-1 to 3C-1) gp21 (SEQ ID NO:21 and SEQ ID NO:22) and (FIGS. 3D-1 to 3D-4 and FIGS. 3E-1 to 3E-4) gp46 (SEQ ID NO:23 and SEQ ID NO:24) regions were sequenced. Fractions above a nucleotide change indicate the frequency of that mutation seen in different clones from an individual patient. For comparison the sequences of the corresponding regions of the HTLV-I-infected cell line, HS-35, derived from a Caribbean patient, and the STLV-I-infected cell line, PtM3, from a pig-tailed macaque (*Macaca nemestrina*) originally imported from Indonesia, are included where data was available. Sites of insertion are as indicated and deletions are represented by an asterisk. Dashed lines are regions where the sequence of the isolate can not be determined because the primers themselves are incorporated into the amplified product. Amino acid changes are shown for regions between the primers.

FIG. 4A to 4E show the nucleotide sequence alignment of the 522-base pair, gp21-encoding region of the env gene amplified from DNA from six Melanesians (HTLV-I Melanesia 1 to 6) and two Polynesians (HTLV-I Bellona 1 and 2), and comparison with the DNA sequence of a Japanese prototype HTLV-I$_{ATK-1}$ (SEQ ID NO:25) (Seiki et al., PNAS USA 1983; 80:3618-3622). The arrow indicates the cleavage site between the carboxy terminus of gp46 and the amino terminus of gp21. There were no deletions or insertions, and none of the point mutations resulted in the introduction of stop codons.

FIGS. 5A to 5C show the comparison of deduced amino acid sequences of the env gene region from a Japanese prototype HTLV-I$_{MT-2}$ (Gray et al., Virology 1991; 177:391-395), two Polynesian strains of HTLV-I (Bellona 1 and 2) and six Melanesian HTLV-I variants (Melanesia 1 to 6). The respective sequences of HTLV-II$_{C344/MO}$ (Shimotohno et al., PNAS USA 1985; 82:3101-3105) and STLV-I$_{macaque}$ (Watanabe et al., Virology 1985; 144:59-65) are also shown. Blanks indicate homologous sequence with prototype HTLV-I$_{MT2}$. Note shared amino acids between the Melanesian HTLV-I variants and HTLV-II (and STLV-I) at positions 305, 328, 330 and 372. The single letter amino acid code was used.

FIGS. 6A to 6B show a hydropathy analysis of the deduced amino acid sequence of the env protein (SEQ ID NO:26). The plot shows a large hydrophobic region and alternating hydrophobic and hydrophilic domains typical of membrane proteins. The positions of the amino acid residues and the values of the hydrophobic indices are shown on the x and y axes, respectively. The cleavage site between the C-terminus of the major envelope glycoprotein gp46 and the N-terminus of the transmembrane protein gp21 is indicated by an arrow.

(FIG. 7A). Relationship based on the regions sequenced from pol, env (gp21, gp46) and tax. (FIG. 7B). Relationship based on sequences from env (gp21, pg46) and tax.

DETAILED DESCRIPTION OF THE INVENTION

Figures 3, 3E, 4:
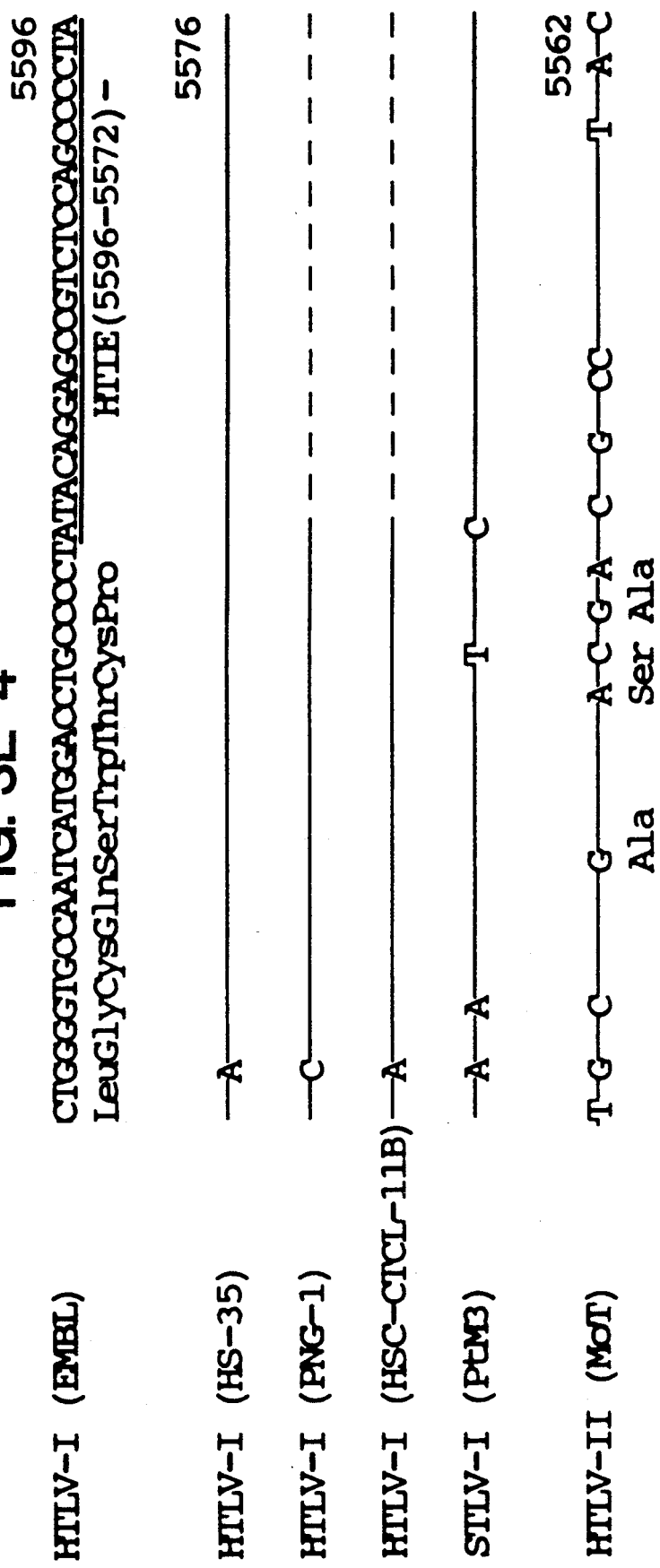

The present invention relates to a cell line, preferably a human T-cell line, persistently infected with a Papua New Guinea (PNG) HTLV-I variant. Cells of the present invention express viral antigens, type C particles and have a low level of reverse transcriptase activity. The inventors have established a human T-cell line, designated PNG-1, derived from peripheral blood mononuclear cells of a healthy New Guinean with the above described characteristics. PNG-1, a CD8 T-cell line, is infected with a HTLV-I variant indigenous to Papua New Guinea, referred to herein as the PNG-1 variant. The establishment of this cell line, the first of its kind from an individual from Papua New Guinea, makes possible the screening of Melanesian populations using a local virus strain.

The present invention further relates to the virus infecting PNG-1 cells. A substantially pure preparation of the infecting PNG-1 variant can easily be isolated from the cell line or a lysate thereof by one skilled in the art without undue experimentation. Unlike strains of HTLV-I from Japan, the West Indies, the Americas and Africa which share≧97% sequence homology, the PNG-1 variant is only about 92% identical to a Japanese prototype HTLV-I (ATK-1) (Seiki et al., PNAS USA 1983; 80:3618–3622) and to HTLV-I strains isolated from Japanese patients with HTLV-I-associated myelopathy (Kinoshita et al., Int. J. Cancer 1991; 47:491–495) and from Jamaican patients with tropical spastic paraparesis (Daenke et al., J. Virol. 1990; 64:1278–1282). The env sequences of the PNG-1 variant, in turn, differs by approximately 4% from that of the variants from Melanesian Solomon Islanders, indicating the existence of new HTLV-I quasispecies. Although the PNG-1 variant lacks close sequence homology with a prototype strain (C344/Mo) of HTLV-II (Shimotohno et al., PNAS USA 1985; 82:3101–3105) and an Asian subtype of STLV-I (Watanabe et al., Virology 1985; 144:59–65), it is somewhat more closely related to HTLV-II than are cosmopolitan prototypes of HTLV-I.

In addition, the present invention relates to antibodies specific for the PNG-1 variant or viral proteins expressed by PNG-1. One skilled in the art using standard methodology can raise monoclonal and/or polyclonal antibodies to the variant or viral proteins expressed by the cells of the present invention without undue experimentation.

The present invention also relates to a vaccine for use in humans to prevent infection with and diseases caused by HTLV-I and related viruses. Diseases to which the present invention relates include, adult T-cell leukemia/lymphoma and tropical spastic paraparesis/HTLV-I-associated myelopathy. A non-infectious antigenic portion of the PNG-1 variant can be delivered to a human in a pharmacologically acceptable vehicle. Antigen preparations for use in the vaccine can take the form of inactivated/attenuated whole virus concentrates, for example, PNG-1 cell lysate, or viral proteins (or fragments thereof). The viral proteins and protein fragments can be produced, for example, by recombinant DNA techniques.

Vaccines of the present invention can also include effective amounts of immunological adjuvants known to enhance an immune response. The non-infectious antigenic portion of PNG-1 variant is in the vaccine in an amount sufficient to induce an immune response against the antigenic portion and thus to protect against infection with and diseases caused by HTLV-I and related viruses. The vaccines can be administered via the intradermal, subcutaneous or intra-muscular route. The vaccination may consist of a single administration or a series of administrations. This will vary depending on several factors, such as the patient's age and condition and the route of administration. These factors are easily assessed by the attending physician and an appropriate vaccination schedule determined therefrom.

PNG-1 and variant-specific peptides thereof can be used in a variety of serological test systems, including but not limited to immunoassay, gel particle agglutination, immunofluorescence, Western immunoblot, radioimmunoprecipitation and antigen-capture assays. (Variant-specific peptides as used herein refer to peptides unique to the Melanesian HTLV-I variants.) Accordingly, the present invention relates to bioassays for use in human medicine. For diagnosis of adult T-cell leukemia/lymphoma, tropical spastic paraparesis/HTLV-I-associated myelopathy or an infection of the causative agent thereof, the presence of antibodies to PNG-1 proteins or the presence of the viral proteins in a biological sample such as, for example, serum or culture fluid, can be determined. Many types of tests, as one skilled in the art will recognize, can be used for detection and bioassays can be performed using standard protocols.

Specifically, in one bioassay of the present invention, antibodies against Papua New Guinea HTLV-I variants are detected with the use of variant-specific peptides. The variant-specific peptides can be isolated from natural sources, recombinantly produced or synthesized using standard automated methods. Suitable peptides include those encoded by variant-specific regions of the env gene sequences, such as, gp46 aa 17–28 and gp21 aa 324–335. Preferred peptides include, ProIleLeuSerPheTyrSerProSerCysCysThr (amino acids 17–28) (SEQ ID NO:1) for the major envelope glycoprotein gp46 and LeuAlaIleGlyThrGlyIleAlaGlyGlyIleThr (amino acids 324–335) (SEQ ID NO:2) for the transmembrane glycoprotein gp21. The peptides are purified such as, by preparative high-performance liquid chromatography. Peptide sequence and purity can be confirmed by amino acid composition and sequence studies.

The variant-specific peptides are used to detect IgG, IgM or IgA antibodies in a biological sample (such as serum or cerebrospinal fluid) using immunoassays. Wells of plates, such as polyvinyl chloride plates, are coated with the peptides. The wells are then coated with an agent to block excess reactive sites, such as 3% bovine serum albumin. The biological sample is then diluted (for example, 1:20) and added to the wells. The antibody-antigen complexes are detected by labelled antibody against human IgG, IgM or IgA. For example, the antibody can be labelled with alkaline phosphatase which causes a change in color detectable by an ELISA reader.

In another assay of the present invention, PNG-1 cells are fixed on a surface and then their membranes are permeabilized, such as with acetone. The fixed cells are contacted with serum from a patient and the presence or absence of the viral protein-antibody complex is then detected using methods well known in the art.

In another assay of the present invention, a surface (i.e., a solid support), for example, a nitrocellulose membrane used in Western blots on which PNG-1 cell lysates or purified virus or variant specific recombinant proteins have been electrotransferred is contacted with a sample, such as serum, from a patient suspected of having disease or infection. The presence of a resulting complex formed between the viral protein(s) and antibodies specific therefor in the serum can be detected by any of the known methods common in the art, such as biotinylated or enzyme-labeled secondary antibodies.

Alternatively, the PNG-1 protein or variant-specific peptide thereof can be bound to an inert particle of, for example, bentonite or polystyrene latex. The particles are mixed with serum from a patient in, for example, a well of a plastic agglutination tray. The presence or absence of antibodies in the patient's serum is determined by observing the settling pattern of the particles in the well.

In a further bioassay of the present invention, the presence or absence of viral nucleic acid in a serum sample is detected. Viral genomic sequences can be amplified (for example, polymerase chain reaction) and detected by, for example, ethidium bromide staining or Southern blot analysis. Confirmation of the specificity of the amplified product may be accomplished by sequencing, or restriction enzyme mapping and hybridization using specific oligoprobes.

Suitable variant-specific primers for env gene amplification include 5'-CCGGCCTCACAATCCCGTTCCCGC-3' (SEQ ID NO:3) and 5'-TGGCGGTCTGGCTAGTCTCC-3' (sense primers) (SEQ ID NO:4) and 5'-AAACGTG-GGAATTAGTGATGTTTA-3' (SEQ ID NO:5) and 5'-CTTGTAGCGCCTTGCATAATCC-3' (SEQ ID NO:6) (antisense primers). The amplified sequences can be detected with an oligoprobe, such as 5'-CAGAC-GAGGCCTTGATCTCC-3'(SEQ ID NO:7).

In another bioassay of the present invention, the presence or absence of PNG-1 variant-specific protein in a serum sample is detected with antibodies. Antibodies of the present invention specific for a virus protein thereof can be coated onto a solid surface such as a plastic and contacted with the serum sample. After washing, the presence or absence of the virus protein from the serum bound to the fixed antibodies is detected such as by addition of a labeled (e.g. enzyme-labeled) antibody specific for the virus.

The present invention further relates to kits for the diagnosis of HTLV-I infections, particularly PNG-I infections. Such kits provide an easy and safe means of diagnosing infections. One kit of the present invention includes variant-specific peptides from the Papua New Guinea variant virus, such as LeuAlaIleGlyThr-GlyIleAla GlyGlyIleThr (SEQ ID NO:2). The kit also includes ancillary reagents suitable for use in detecting the presence of antibody-peptide complexes.

Another diagnostic kit of the present invention contains oligonucleotide primers specific for the Papua New Guinea variant virus and ancillary reagents suitable for DNA amplification and DNA detection. Suitable primers include, 5'-CCGGCCTCACAATCCCGTTCCCGC3' (SEQ ID NO:8) and 5'-TGGCGGTCTGGCTAGTCTCC-3' (SEQ ID NO:10) (sense primers) and 5'-AAACGTG-GGAATTAGTGATGTTTA-3' and 5'-CTTGTAGCGCCTTGCATAATCC-3' (SEQ ID NO:11) (antisense primers). For example, one such kit contains PCR reaction mix (Tris HCl at pH 8.3, KCl, $MgCl_2$, dNTPs and AmpliTaq DNA polymerase), and primers for routine PCR and for nested PCR. The PCR reaction is carried out at 94° C. for 5 min., followed by 35 cycles of 94° C. for 1 min.., 55° C. for 1 min. and 72° C. for 3 min. PCR is then continued at 72° C. for 7 minutes and cooled to 4° C. until separation. The amplified product can be detected using the standard methods. For example, agarose gel electrophoresis and ethidium bromide staining can be employed. Alternatively, the amplified product can be detected using Southern blot analysis with a full-length HTLV-I probe or internal oligonucleotide probes, such as, 5'-CAGAC-GAGGCCTTGATCTCC-3' (SEQ ID NO:7), labeled with $^{32}p$ and high stringency wash conditions.

The following examples are given to further illustrate the present invention without being deemed limitative thereof.

EXAMPLES

Statement of Deposit

The human T-cell line PNG-1 was deposited on Aug. 14, 1990 at the American Type Culture Collection (Rockville, Md.), in accord with the requirements of the Budapest Treaty. The cell line PNG-1 has been assigned the ATCC accession number CRL 10528.

Study Population

The Hagahai, a 260-member, hunter-horticulturist group which made first sustained contact with government and missionary workers in 1984 (Jenkins, Soc. Sci. Med. 1988; 26:997–1006; and Jenkins et al., Hum. Ecol. 1989; 17:27–57) occupy an area totalling 750 $km^2$ along the northern banks of the Yuat River Gorge in Madang Province of Papua New Guinea. Linguistically, the Hagahai have been classified into the Piawi family, tentatively assigned to the Sepik-Ramu phylum, a non-Austronesian language group.

Like the highland and Sepik groups, the Hagahai lack the HLA-A2 antigen associated with recent Austronesian admixture, suggesting that they predate the last Austronesian migration into Papua New Guinea, currently dated to 5400 B. P. (Jenkins, Soc. Sci. Med. 1988;26:997–1006; Jenkins et al., Hum. Ecol. 1989;17:27–57; and Bhatia et al., Hum. Biol. 1989;61:45–64).

As verified by strict Western immunoblot criteria (Centers for Disease Control, MMWR 1988; 37:736-747), an HTLV-I seroprevalence of 14% was found among 120 Hagahai bled between February 1985 and January 1988 (Yanagihara et al., J. Infect. Dis. 1990; 162:649–654). A high frequency of indeterminate Western immunoblots was also found among ELISA-positive Hagahai.

Also studied were six unrelated Solomon Islanders (including two residents of Bellona Island) from three of whom HTLV-I-infected T-cell lines were derived (Yanagihara et al., Jpn. J. Cancer Res. 1991; 82:240–244; and U.S. application Ser. No. 07/662,368, filed Feb. 28, 1991) (Table II). Bellona (population 650), known also as Mu Ngiki (or "small island"), is, along with Rennell, Tikopia, Anuta (Cherry Island), Sikaiana (Stewart Island) and Ontong Java (Lord Howe Atoll), a Polynesian Outlier within the Solomon Islands. It lies 180 km south of Guadalcanal and is populated by Polynesians. Genetic distance analysis, based on allele frequencies of ABO blood groups, red cell enzymes and serum proteins, indicate that the inhabitants of Bellona are distinct from Melanesians despite their close geographical proximity (Blake et al., Am. J. Phys. Anthropol. 1983; 62:343–361).

PNG-1 Virus Isolation

In May, 1989, 25 ml of heparinized blood was drawn from each of 24 Hagahai men and women, of whom 7 had confirmatory and 17 had indeterminate HTLV-I Western immunoblots. Blood samples were collected in the field, and were rushed to the Papua New Guinea Institute of Medical Research in Goroka, where they were processed in a laboratory in which HTLV-I and other human retroviruses had not previously been handled. Lymphocytes were separated using Sepracell (Supratech Corporation, Inc., Oklahoma City, Okl.), then washed twice with phosphate buffered saline (pH 7.4) before being incubated in RPMI 1640 (M.A. Bioproducts, Inc., Walkersville, Md.) supplemented with 20% (vol/vol) heat-inactivated fetal bovine serum, 4 mM L-glutamine, 50 µg of gentamicin per ml and 2 µg of phytohemagglutinin (PHA) per ml (Wellcome Diagnostics, Dartford, England). Following mitogen stimulation for two days, cells were maintained in medium containing 10% (vol/vol) interleukin 2 (IL-2) (Advanced Biotechnologies, Inc., Columbia, Md.). Except for a 60-hr period while being transported from Goroka to the National Institutes of Health in Bethesda, the cultures were incubated at 37° C. in a humidified 5% $CO_2$ atmosphere. Growth medium was changed twice weekly. Cultures were examined periodically for HTLV-I antigens by indirect immunofluorescence, for reverse transcriptase activity, and for viral particles by electron microscopy.

Re-isolation Attempts

Re-isolation attempts were conducted in an HTLV-I-free laboratory on lymphocytes from 15 Hagahai. Lymphocytes, preserved in 10% DMSO and stored in liquid nitrogen, were rapidly thawed in a 37° C. water bath and were stimulated with PHA, as described above. Cells were then co-cultivated with approximately $2 \times 10^6$ PHA-stimulated umbilical cord blood mononuclear cells obtained from healthy Caucasian neonates (Advanced Biotechnologies, Inc.), who lacked evidence of HTLV-I infection as determined by the polymerase chain reaction. Cultures were maintained with growth medium supplemented with IL-2. Fresh PHA-stimulated cord mononuclear cells were added, as needed, to maintain the cell density at $10^6$ per ml. Cells were examined weekly for viral antigen by immunofluorescence.

Indirect Immunofluorescence Test

Cultured lymphocytes, spotted onto 10-well slides (Cell-line Associates, Newfield, N.J.) and fixed with cold acetone for 10 min, were examined for the expression of HTLV-I antigens by the indirect immunofluorescent antibody technique, using monoclonal antibodies against HTLV-I p19 (Pan-Data Systems, Inc., and Cambridge Biotech Corp., Rockville, Md.) and p24 (Cambridge Biotech Corp.); rabbit antiserum prepared against native p24 protein and against synthetic peptides of the C-terminus of gp46 (generously provided by Steve S. Alexander and Erik Lillehoj); sera from rabbits experimentally infected with strains of HTLV-I isolated from Colombia; and sera from Colombian and Chilean patients with virologically confirmed tropical spastic paraparesis/HTLV-I-associated myelopathy (Cartier-Rovirosa et al., Lancet 1989; i: 556–557; and McKhann et al., J. Infect. Dis. 1989; 160:371–379). Virus-specific antibodies were then detected using either rhodamine-labeled goat antibodies against mouse or rabbit IgG F(ab')2 (Accurate Chemical & Scientific Corp., Westbury, N.Y.), or fluorescein isothiocyanate-labeled goat antibodies against human IgG (Cappel Laboratories, Inc., Cochranville, Pa.). Incubations were performed in a humidified chamber at 37° C. for 30 min, and slides were washed with 0.01M phosphate buffered saline (pH 7.2). Appropriate dilutions of mouse, rabbit and human negative control sera and HTLV-I infected (MT-2 cells) (Miyoshi et al., Nature 1981; 294:770–771) and uninfected cells (MOLT-3) (American Type Culture Collection, Rockville, Md.) were included in each test. Fluorescence was observed using a Leitz epifluorescence microscope.

Analysis of Viral Proteins

Cell lysates were prepared by gently mixing $50 \times 10^6$ cells in 2 ml 0.1M Tris-HCl (pH 7.4) containing 0.5% sodium deoxycholate (Sigma Chemical Co., St. Louis, Mo.), 0.5% Triton X100 and 0.05% sodium dodecyl sulfate at 4° C. for 30 min. Lysates were clarified by centrifugation at 35,000 rpm (100,000 g) in a Beckman 50.2 Ti rotor for 1 hr. The supernatant was then mixed with sample buffer, and viral proteins were separated by electrophoresis on sodium dodecyl sulfate/polyacrylamide gels (Laemmili, Nature 1970;227:680–685) Proteins were transferred electrophoretically to nitrocellulose membranes (Schleicher & Schuell, Dassel, FRG) in 25 mM Tris, 192 mM glycine and 20% methanol at 100 v for 1 hr. at 4° C. Membranes were blocked for 2 hrs. at room temperature with 50 mM Tris-HCl (pH 7.4) and 0.85% NaCl containing 5% fat-free dry milk, then reacted overnight with autologous sera, with sera from Colombian and Chilean patients with virologically confirmed HTLV-I myeloneuropathy (Cartier-Rovirosa et al., Lancet 1989;i:556–557; and McKhann et al., J. Infect. Dis. 1989;160:371–379) and from rabbits experimentally infected with a Colombian isolate (strain 394) of HTLV-I, and with monoclonal and polyclonal sera directed against HTLV-I p19, p24 and gp46. As controls, sera from HTLV-I-seronegative individuals, rabbits and mice were tested simultaneously. Membranes were incubated successively with either biotinylated goat antibodies against human IgG (H&L) and avidin-horse radish peroxidase or alkaline phosphatase-labeled goat antibodies against rabbit or mouse IgG F(ab')2. Color was developed using 4-chloro-1-naphitol (Kirkregard & Perry Laboratories, Inc., Gaithersburg, Md.) or nitroblue tetrazolium (330 µg per ml) and 5-bromo-4-chloro-3-indolylphosphate (166 µg per ml) (Sigma), respectively.

Polymerase Chain Reaction. Genomic DNA was isolated from approximately $25 \times 10^6$ cells (PNG-1, MT-2 and MOLT-3) using a non-organic method (Oncor, Gaithersburg, Md.). One microgram of DNA was then amplified using oligonucleotide primers, synthesized on a PCR-Mate DNA synthesizer (Applied Biosystems), which were specific for env, gag and tax sequences of ATK-1, a prototype Japanese strain of HTLV-I (Seiki et al., PNAS USA 1983; 80:3618–3622). The reaction mixture consisted of 50 mM KCl, 10 mM Tris-HCl (pH 8.3), 1.5 mMMgCl$_2$, 0.01% gelatin, 0.05% Nonidet P-40, 0.2 mM each dATP, dCTP, dTTP and dGTP, 1 µM each oligonucleotide primer, and 2.5U of TaqDNA polymerase (Perkins-Elmer Cetus, Norwalk, Ct.). Following denaturation at 93° C. for 4 min, the reaction mixtures were cycled 35 times at 93° C. for 1 min, 55° C. for 2 min and 72° C. for 3 min. After one round of amplification with env primers, products were further amplified using "nested" primers. Amplified DNA was size-fractionated by agarose gel electrophoresis and transferred to nylon membranes for hybridization using oligoprobes or a full-length HTLV-I probe labeled with $^{32}P$.

Restriction Endonuclease Analysis

Genomic DNA, extracted from PNG-1, MT-2 and MOLT-3 cells, was digested with several restriction endonucleases (EcoRI, PstI, SacI, HindIII). The digested DNA was separated on a 0.8% agarose gel, transferred onto Nylon membrane (Schleicher & Schuell) and hybridized with a full-length HTLV-I genomic probe labeled with $^{32}P$.

Cytofluorographic Analysis

The surface phenotype of PNG-1 cells was determined by cytofluorographic analysis (Becton-Dickinson), using monoclonal antibodies directed against T- restricted (CD2, CD3, CD4, CD7 and CD8) and B-restricted (CD19 and CD20) antigens.

Electron Microscopy

Cells were centrifuged at 1000 rpm for 10 min, and pellets were fixed in 2% glutaraldehyde for 2 hrs. at 4° C., postfixed in 1% osmium tetroxide for 2 hrs., dehydrated through a graded series of ethanol and propylene oxide and embedded in Embed (Electron Microscopy Sciences, Fort Washington, Pa.). Ultrathin sections, stained with lead citrate and uranyl acetate, were examined using a Hitachi H7000 transmission electron microscope at 75 kV.

One culture, designated PNG-1, derived from a 20-year old Hagahai man, who had IgG antibodies against HTLV-I gag and env-encoded proteins by Western immunoblot, exhibited virus-specific fluorescence in approximately 1% of cells at two weeks, but cell growth remained sluggish for five months, with no increase in the percentage of viral antigen-bearing cells. Consequently, the lymphocytes were co-cultivated with newly acquired MOLT-3 cells (American Type Culture Collection, Rockville, Md.). This resulted in the establishment of a T-cell line which grew rapidly, but remained dependent on exogenous interleukin 2. The percentage of cells expressing viral antigen, as determined by indirect immunofluorescence, increased to more than 85% at 39 days following co-cultivation with MOLT-3 cells (FIGS. 1A to 1B).

Like some HTLV-I-infected T-cell lines, mature viral particles resembling HTLV-I were found only rarely in extracellular spaces of PNG-1 cells, by thin-section electron microscopy (FIG. 2). However, lysates of PNG-1 cells, analyzed by Western immunoblot, exhibited virus-specific bands at 15, 19, 24, 46 and 53 kilodaltons, using sera from Colombian and Chilean patients with virologically confirmed HTLV-I myeloneuropathy and from rabbits experimentally infected with HTLV-I. Moreover, HTLV-I sequences were detected in DNA extracts from PNG-1 cells by polymerase chain reaction (PCR), using oligonucleotide primers specific for gag, env and tax sequences of ATK-1, a prototype strain of HTLV-I.

Analysis of PNG-1 pol, pX and env Genes

PNG-1 was more extensively compared with other HTLV-I and HTLV-II isolates to determine the variability of PNG-1 from cosmopolitans prototype strains of HTLV-I (see Table I below).

PCR amplification and subsequent liquid hybridization using primer pairs and detectors to different regions of the HTLV genome were performed on DNA from four HTLV-I and one HTLV-II-infected cell lines, as previously described (Abbott et al., J. Infect. Dis. 1988; 158:1158–1159). Primers specific for four different regions of the HTLV-I genome and two corresponding regions of the HTLV-II genome were employed to amplify target DNA which was subsequently cloned into the M13mp18 vector and sequenced. The linker sequence ACAGGTACCTGCAGATCTAGA (5'-3') (SEQ ID NO:12), which contains a restriction site for Kpn-I was synthesized on the 5' end of the positive strand primers while the linker sequence TACGAGCTCGCGAATTCATGA (5'-3') (SEQ ID NO:13), which possesses a Sst-I restriction site, was added to the 5' end of the negative strand primers. Amplified DNAs and the M13mp18 vector DNA were digested with both Kpn-I and Sst-I and then ligated together with T4 ligase. After hybridization with end-labelled probes for each respective primer pair, the DNA from each plaque was sequenced by the dideoxy nucleotide termination method.

DNA from the HTLV-I-infected cell lines PNG-1 and HSC-CTCL-11B was amplified and sequenced in specific regions of the pol, pX, and env (gp21 and gp46) genes. In addition, DNA from the cell line MoT and from two HTLV-II-infected patients (RW and FF) was amplified in equivalent regions of the pol and pX genes.

Input DNA from each isolate was normalized to 10,000 copies. The isolate, HSC-CTCL-11B, was used to verify the efficiency of each set of primers and probe. This isolate could be consistently detected at an input of 10 copies of HTLV-I DNA for all except one HTLV-I primer pair described, thereby demonstrating their sensitivity.

Oligonucleotides were named by a two letter initial for HTLV (HT) followed by the number of the designated virus (I or II), then by an initial for the gene or region of the indicated virus with the numbered position in the genome (EMBL system for HTLV-I and Shimotohno et al. for HTLV-II), and finally with a "+" or "−" to indicate the strand and a "d" to indicate

TABLE I

PCR results using various HTLV-I/II primers on different HTLV-I or HTLV-II isolates.

| HTLV-II Primers | Prove | Region | HTLV-I isolates PNG-1 | HSC-CTCL 11B | HUT 102B2 | MT-2 | isolate MoT |
|---|---|---|---|---|---|---|---|
| HTIL(490–515)+/HTIL(655–630)− | HTIL(564–596) + d | LTR | − | + | + | + | − |
| HTIG(863–886)+/HTIG(1397–1375)− | HTIG(981–1023) + d | GAG | +* | +* | +* | +* | − |
| HTIG(1215–1235)+/HTIG(1393–1370)− | HTIG(1238–1277) + d | " | − | + | + | + | − |
| HTIG(1388–1411)+/HTIG(1660–1641)− | HTIG(1451–1412) + d | " | +* | + | + | + | − |
| HTIG(1423–1444)+/HTIG(1560–1537)− | HTIG(1475–1507) + d | " | + | + | + | + | − |
| HTIP(2801–2820)+/HTIG(3037–3018)− | HTIP(2821–2860) + d | POL | +* | + | +* | +* | − |
| HTIP(3365–3384)+/HTIP(3483–3465)− | HTIP(3460–3426) + d | " | − | + | + | + | − |
| HTIP(4757–4778)+/HTIP(4942–4919)− and HTIIP(4735)–4736)+/HTIIP(4920–4897)− | HTIP(4870–4902) + d and HTIP(4848–4880) + d | " | + | + | + | + | + |
| | HTIP(4825–4850) + d | " | + | + | + | + | − |
| | HTIIP(4880–4898) + d | " | − | − | − | − | + |
| HTIE(5228–5247)+/HTIE(5596–5572)− | HTIE(5305–5271) + d | ENV | + | + | +* | − | − |
| HTIE(5270–5292)+/HTIE(5540–5521)− | HTIE(5301–5340) + d | " | +* | + | +* | +* | − |
| HTIE(6293–6324)+/HTIE(6527–6498)− | HTIE(6330–6368) + d | " | + | + | +* | +* | − |
| HTIpX(7358–7377)+/HTIpX(7516–7596)− and HTIIpX(7248–7267)+/HTIIpX(7406–7386)− | HTIpX(7447–7468) + d and HTIIpX(7337–7476) + d | pX | + | + | + | + | + | a detector. PNG-1, HSC-CTCL-11B, HUT 102B2, and MT-2 are cell lines containing HTLV-I isolates from a Papua New Guinean, a Liberian of American slave descent, an African American and a Japanese, respectively. Input DNA from each isolate was normalized to 10,000 copies. A "+" symbol represents a band on liquid hybridization after 30 or 60. cycles of PCR. A "−" symbol represents no presence of hybridization after 30 or 60. cycles of PCR.

As seen from Table I, while PNG-1 belongs to the HTLV-I subgroup, it varies considerably from cosmopolitan prototypes of HTLV-I [MT-2 (Miyoshi et al., Nature 1981; 294:770-771), HUT 102B2 (Poiesz et al., PNAS USA 1980; 77:7415-7419), and HSC-CTCL-11B (Ehrlich et al., Am. J. Hematol. 1989; 30:128-139).

A protein-coding region in the tax gene (ORF pX-II) of HTLV-I was sequenced for PNG-1 and HSC-CTCL-11B and the corresponding HTLV-II region for MoT (Kalyanaraman et al., Science 1982; 218:571-573; and Shimotohno et al., PNAS USA 1985; 82:3101-3105) and two other HTLV-II isolates (RW and FF) (FIGS. 3A-1 to 3A-4). Published sequences for a prototype Japanese HTLV-I isolate (ATK-1) (Seiki et al., PNAS USA 1983; 80:3618-3622) (EMBL numbers are identical to the sequence of Seiki et al. for these regions), a Caribbean HTLV-I (HS-35) (Malik et al., J. Gen. Virol. 1988; 69:1695-1710), and STLV-I (Watanabe et al., Virology 1985; 144:59-64) were also included for comparison. Very little sequence variation was found among the isolates in this pX region. The HTLV-II isolates vary only 15% from the Japanese isolate as compared to 40% for the entire proviral DNA sequence. Others have also found strong conservation in the pX gene (Shimotohno et al., PNAS USA 1985; 82:3101-3105; and Shaw et al., PNAS USA 1984; 81:4544-4548) which is evidently maintained by the importance of its transactivating function. Two variants within the HSC-CTCL-11B isolate were identified here which is in agreement with previous data indicating two dominant proviral integrates in this cell line (Ehrlich et al., Am. J. Hematol. 1989; 30:128-139). From these data PNG-1 is most closely related to the HTLV-I family of retroviruses.

Strong conservation of the pol gene was also expected based on the importance of reverse transcription in the viral life cycle. Whereas there is a 36% difference between the prototype sequences of HTLV-I (ATK-1) and HTLV-II (MOT), there is strong conservation of sequence among the Japanese (ATK-1), Caribbean (HS-35), and Liberian (HSC-CTCL-11B) HTLV-I isolates and also among the HTLV-II isolates (FIGS. 3B-1 to 3B-4). By contrast, PNG-1 possessed 5 amino acid changes in the amplified region and at the nucleotide level, it varied by 8.6% from the prototype Japanese HTLV-I sequence and by 9.3% from the Caribbean, thereby establishing PNG-1 as a unique and distinct HTL-VI variant. The variation seen here far exceeds the inherent mutation rate involved in cloning of amplified DNA (Meyerhans et al., Cell 1989; 58:901-910).

Sequencing of a region of the transmembrane portion of the env gene (gp21), which includes the coding region of the putative immunosuppressive peptide (Ruegg et al., J. Virol. 1989; 63:3250-3256), indicated that PNG-1 was approximately 9.7% different from the prototype Japanese HTLV-I (ATK-1). However, 4 transitions from deoxyadenosine to deoxythymidine were noted that were conserved in all the sequences depicted, including HTLV-II and STLV-I (FIGS. 3C-1 to 3C-4). In addition, in sequencing this region of the HTLV-I env gene from 20 North American isolates, these 4 transitions were found to be conserved. Others have also described conservation of these changes in 8 of 8 Japanese adult T-cell leukemia/lymphoma patients (Kinoshita et al., Int. J. Cancer 1991; 47:491-495), in 11 of 12 HTLV-I-associated myelopathy patients (Kinoshita et al., Int. J. Cancer 1991; 47:491-495) as well as in 12 of 12 Jamaican tropical spastic paraparesis patients (Daenke et al., J. Virol. 1990; 64:1278-1282). Since these transitions are not conserved based on geography, species, or disease and 3 of the 4 cause amino acid substitutions, sequencing error of the original ATK-1 clone may account for the discrepancy.

A deletion in 6 independent env (gp21) clones of PNG-1 resulted in an altered reading frame of the transmembrane protein. One PNG-1 env (gp21) clone of 6 contained a deoxyguanidine that is not present in the others. Since the env gene FIGS. 3C-1 to 3C-4, FIGS. 3D-1 to 3D-4 and FIGS. 3E-1 to 3E-4) is more variable overall than the tax or pol genes, quasispecies (Shaw et al., PNAS USA 1984; 81:4544-4548) may exist as defined by gp21 and gp46. In fact, two distinct gp46 clones for PNG-1 were found, indicating the presence of quasispecies. The phenomenon of multiple variants within a single individual has been described for both HIV (Saag et al., Nature 1988; 354:440-444; and Goodenow et al., J. AIDS 1989; 2:344-352) and HTLV-I (Daenke et al., J. Virol. 1990; 64:1278-1282).

FIGS. 3D-1 to 3D-4 and 3E-1 to 3E-4 show the sequence comparison of the HTLV variants from the 5' region of the env gene which encodes the extracellular membrane protein gp46. It was expected that portions of this gene region would be highly variable since the protein it encodes is under continuous selective pressure of the patient's immune system (Paquette et al., PNAS USA 1989; 86:3896-3900) and provides a target for neutralizing antibodies and antibody-dependent cellular cytotoxicity, while other portions would be strongly conserved since extracellular env proteins determine cell tropism (Paquette et al. 1989; PNAS USA, 86:3896-3900). Indeed, in FIGS. 3D-1 to 3D-4 and 3E-1 to 3E-4 one can see stretches of variability from a consensus sequence, interrupted by conserved regions, for an overall variation of 6.9% for PNG-1 from cosmopolitan prototype.

PNG-1 contained a deletion near the 5' end of gp46 (as indicated in FIG. 3D1) which changed the reading frame, but an insertion occurred shortly thereafter that restored the protein to the consensus frame. This specific region of the gp46 (EMBL No. 5250-5265) exhibited considerable variation in the STLV-I isolate and HTLV-II isolates, as well as the Caribbean and Liberian HTLV-I isolates. This nucleotide sequence and its corresponding peptide may be valuable in typing virus variants and for diagnosis of infection by creating specific oligonucleotide primers for PCR or specific peptides for ELISA and Western blot immunoassay.

Sequence Analysis of PNG-1

Further sequence analysis was done to compare PNG-1 env gene with other Melanesian and Polynesian HTLV-I isolates. DNA was isolated from uncultured (fresh) peripheral blood mononuclear cells (PBMC), PBMC in culture for 4 weeks and HTLV-I infected T-cell lines derived from the Hagahai (PNG-1) (Yanagihara et al., N. Engl. J. Med. 1990; 323:993-994; and Yanagihara et al., PNAS USA 1990; 88:1146-1150)

and Solomon Islanders (SI-1, SI-3, SI-5) (Yanagihara et al., Jpn. J. Cancer Res. 1991; 82:240–244; and Yanagihara et al., J. Infect. Dis. 1991, in press) using a non-organic method (Oncor, Gaithersburg, Md.), and was subjected to PCR. (See Table II below.) Oligonucleotide primer pairs derived from highly conserved regions of the HTLV-I env gene (sense strand, 5'-TTTGAGCGGCCGCTCAAGC-TATAGTCTCCTCCCCTG-3' (SEQ IN NO:14); antisense strand, 5'-ACTTAGAATTCGGAGGTGTC-GTAGCTGACGGAGG-3' (SEQ ID NO:5) and containing NotI and EcoRI restriction sites (underlined), respectively, were employed. The 522-base pair amplified region, which corresponded to bases 6046 to 6567 (equivalent to EMBL no. 6068 to 6589 of prototype HTLV-I$_{ATK-1}$), encompassed the cleavage site of the envelope precursor protein and included nearly the entire coding region for the transmembrane glycoprotein gp21.

Amplified DNA was cloned into the NotI and EcoRI restriction sites of the Bluescript vector, then transformed into HB101 competent cells. Recombinant clones were screened by hybridization, under high stringency conditions, with a $^{32}$P-end-labeled internal oligonucleotide probe (5'-CAGACGAGGCCTT-GATCTCC-3' (SEQ ID NO:16), corresponding to bases 6313 to 6332). Nucleotide sequences of one to three clones from each DNA sample were determined by the dideoxynucleotide termination method, and sequence analysis was facilitated by using the Microgenie program (Beckman).

the degree of sequence variation was identical (or nearly so) whether the DNA was extracted from uncultured (fresh) PBMC or PBMC cultured for four weeks or from T-cell lines derived from Melanesians (PNG-1, SI-1, SI-5), indicating that these variant sequences did not result from selection during prolonged maintenance of a few virus-infected cells in culture over many months.

The near identity (only a single base difference) between the two Papua New Guinean HTLV-I strains (Melanesia 1 and 2) was not unexpected, since they originated from a mother and her son, and is consistent with transmission from mother-to-child during infancy. Similarly, the env gene nucleotide sequences of the HTLV-I variants from the four Melanesian Solomon Islanders (Melanesia 3 to 6) exhibited a high degree of homology with each other, but they differed from the two HTLV-I strains from Papua New Guineans (Melanesia 1 and 2) by nearly 4% (Table III). Interestingly, the env sequence of the Melanesian Solomon Islander with HTLV-I myeloneuropathy (Melanesia 6) was as divergent (7.5%) from cosmopolitan prototype HTLV-I as the other Melanesian HTLV-I variants, suggesting that these variant viruses are capable of causing disease. By contrast, the env sequences in two Polynesians from Bellona were closely related to cosmopolitan prototype HTLV-I, differing by only 2.3% and 3.1% (Table III and FIGS. 4A to 4E), which is similar to that found in HTLV-I strains from Zaire, which hitherto exhibited the highest variability of 3.4%.

All Melanesian HTLV-I isolates lacked close se-

TABLE II

Demographic features of six Melanesians and two Polynesians in whom a 522-bp region of the HTLV-I env gene was amplified and sequenced.

| Patient | Age/Sex | Origin | Island/Region | Virus | Provirus amplified from |
|---|---|---|---|---|---|
| 1 | 21M | Papua New Guinea | Madang | HTLV-I Melanesia 1 | T-Cell line (PNG-1), Fresh PBMC |
| 2 | 60F | | Madang | HTLV-I Melanesia 2 | Cultured PBMC |
| 3 | 40F | Solomon Islands | New Georgia | HTLV-I Melanesia 3 | T-Cell line (SI-1) |
| 4 | 60F | | Guadalcanal | HTLV-I Melanesia 4 | Fresh PBMC |
| 5 | 58M | | Guadalcanal | HTLV-I Melanesia 5 | T-Cell line (SI-5) |
| 6 | 38M | | Guadalcanal | HTLV-I Melanesia 6 | Cultured PBMC |
| 7 | 60F | | Bellona | HTLV-I Bellona 1 | T-Cell line (SI-3), Fresh PBMC |
| 8 | 50F | | Bellona | HTLV-I Bellona 2 | Cultured PBMC |

Alignment and comparison of the nucleotide sequence of each provirus with the published genomic sequence of a prototype Japanese HTLV-I$_{ATK-1}$ (Seiki et al., PNAS USA 1983; 80:3618–3622) revealed the existence not only of highly divergent variants of HTLV-I in Melanesia but of new quasispecies (or genetically distinct viral populations) within this HTLV-I variant (FIGS. 4A to 4E). A marked divergence of approximately 8% (39 to 43 base substitutions in the 522-bp region sequenced) was found in the six Melanesian HTLV-I variants (Table III). For any individual, quence homology with a prototype strain (C344/Mo) of human T-lymphotropic virus type II (HTLV-II) (Shimotohno et al., PNAS USA 1985; 82:3101–3105) and an Asian subtype of simian T-lymphotropic virus type I (STLV-I), isolated from a pig-tailed macaque (Macaca nemestrina) originally imported from Indonesia (Watanabe et al., Virology 1985; 144:59–65) (Table III). However, the Melanesian HTLV-I variants exhibited slightly closer homology to HTLV-II than did cosmopolitan prototype strains of HTLV-I (including the viruses from Bellona).

TABLE III

| | Nucleotide Sequence Homology | | | | | |
|---|---|---|---|---|---|---|
| Virus Strain5 | HTLV-I ATK-1 | HTLV-I Bellona 2 | HTLV-I Bellona 1 | HTLV-I Melanesia 6 | HTLV-I Melanesia 5 | HTLV-I Melanesia 4 |
| HTLV-IATK-1 | 0 | | | | | |
| HTLV-IBellona 2 | 3.1 | 0 | | | | |
| HTLV-IBellona 1 | 2.3 | 0.8 | 0 | | | |
| HTLV-IMelanesia 6 | 7.9 | 8.2 | 7.5 | 0 | | |
| HTLV-IMelanesia 5 | 7.5 | 7.9 | 7.1 | 1.1 | 0 | |
| HTLV-IMelanesia 4 | 7.5 | 7.9 | 7.1 | 1.1 | 0 | 0 |
| HTLV-IMelanesia 3 | 7.7 | 8 | 7.3 | 1 | 0.6 | 0.6 |
| HTLV-IMelanesia 2 | 8.2 | 9 | 8.2 | 3.8 | 3.4 | 3.4 |

TABLE III-continued

| Nucleotide Sequence Homology | | | | | | |
|---|---|---|---|---|---|---|
| HTLV-IMelanesia 1 | 8.2 | 9 | 8.2 | 3.8 | 3.4 | 3.4 |
| STLV-Imacaque | 10.5 | 10.9 | 10.2 | 10.5 | 10.2 | 10.2 |
| HTLV-IIC344/Mo | 30.6 | 31 | 30.3 | 28.5 | 27.5 | 27.5 |

| Virus Strain5 | HTLV-I Melanesia 3 | HTLV-I Melanesia 2 | HTLV-I Melanesia 1 | STLV-I macaque | HTLV-II C344/Mo |
|---|---|---|---|---|---|
| HTLV-IATK-1 | | | | | |
| HTLV-IBellona 2 | | | | | |
| HTLV-IBellona 1 | | | | | |
| HTLV-IMelanesia 6 | | | | | |
| HTLV-IMelanesia 5 | | | | | |
| HTLV-IMelanesia 4 | | | | | |
| HTLV-IMelanesia 3 | 0 | | | | |
| HTLV-IMelanesia 2 | 3.6 | 0 | | | |
| HTLV-IMelanesia 1 | 3.6 | 0 | 0 | | |
| STLV-Imacaque | 10 | 11.7 | 11.7 | 0 | |
| HTLV-IIC344/Mo | 27.7 | 28.5 | 28.5 | 29.3 | 0 |

Homology is expressed as percent divergence from the cosmopolitan prototype HTLV-I$_{ATK-1}$.

The nucleotide changes identified in the HTLV-I variants from Melanesia corresponded primarily to single base substitutions within a given codon, the vast majority (85%) occurring at the third position, resulting in no amino acid change (see FIGS. 5A to 5C). Thus, at the level of the deduced amino acid sequence, the Melanesian HTLV-I variants differed by 2.3% to 4.0% (4 to 7 amino acids in 174 residues) from the prototype Japanese HTLV-I$_{MT-2}$. Half of the nucleotide substitutions resulting in codon-altering amino acid changes were conservative and were restricted to the C-terminus and the N-terminus of the gp46 and gp21 envelope glycoproteins, respectively (FIGS. 5A to 5C). No nonconservative amino acid changes occurred in the region containing the immunosuppressive peptide.

Figure 6B:
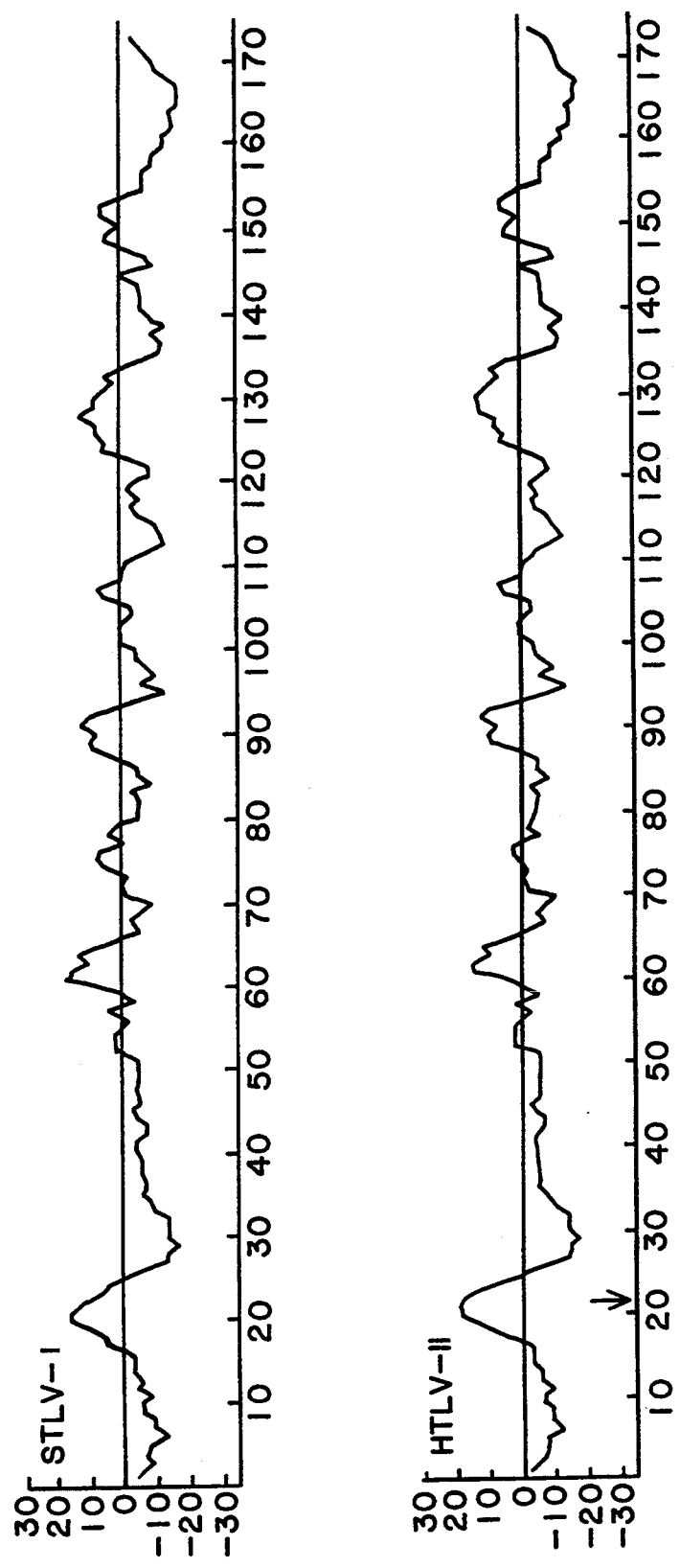

As evidenced by hydropathy analyses (see FIGS. 6A and 6B), the envelope structure of these HTLV-I variants, like that of prototype HTLV-I, is under tight genetic constraint and few amino acid changes seem compatible with HTLV-I replication and infectivity. To what extent the use of peptides, encoded by the unique gene sequences of the Melanesian HTLV-I variants, will obviate the serodiagnostic problems encountered in Melanesia is uncertain (Yanagihara et al., Lancet 1991; 337:617–618).

Evolutionary Relationship

To deduce the evolutionary relationships among members of the HTLV family, dendrograms were constructed using the unweighted pair-group method of assortment (UPGMA) (Nei, Frontiers of Biology Eds. Neuberger and Tatum, 199–202 1975) for comparing the divergence pattern for an HTLV-II isolate (MOT) (Kalyanavaman et al., Science 1982; 218:571–573) from a North American patient with a variant of hairy T-cell leukemia, an STLV-I isolate from Asia (PtM3) (Watanabe et al., Virology 1985; 144:59–64), and HTLV-I isolates from an asymptomatic Papua New Guinean (PNG-1), an African with adult T-cell leukemia/lymphoma (EL) (Paine et al., Virology 1991; 182:111–123) a Caribbean with adult T-cell leukemia/lymphoma (HS-35) (Malik et al., J. Gen. Virol. 1988; 69:1695–1710), a Liberian of American slave descent with ATLL (HSC-CTCL-11B) (Ehrlich et al., Am. J. Hematol. 1989; 30:128–139), a North American with adult T-cell leukemia/lymphoma (CH) (Paine et al., Virology 1991; 182:111–123), a Japanese with adult T-cell leukemia/lymphoma (ATK) (Seiki et al., PNAS USA 1983; 80:3618–3622), and a Japanese with HTLV-I-associated myelopathy (H5) (Tsujimoto et al., Mol. Biol. Med. 1988; 5:29–42) (See FIG. 7).

Figure 7A:
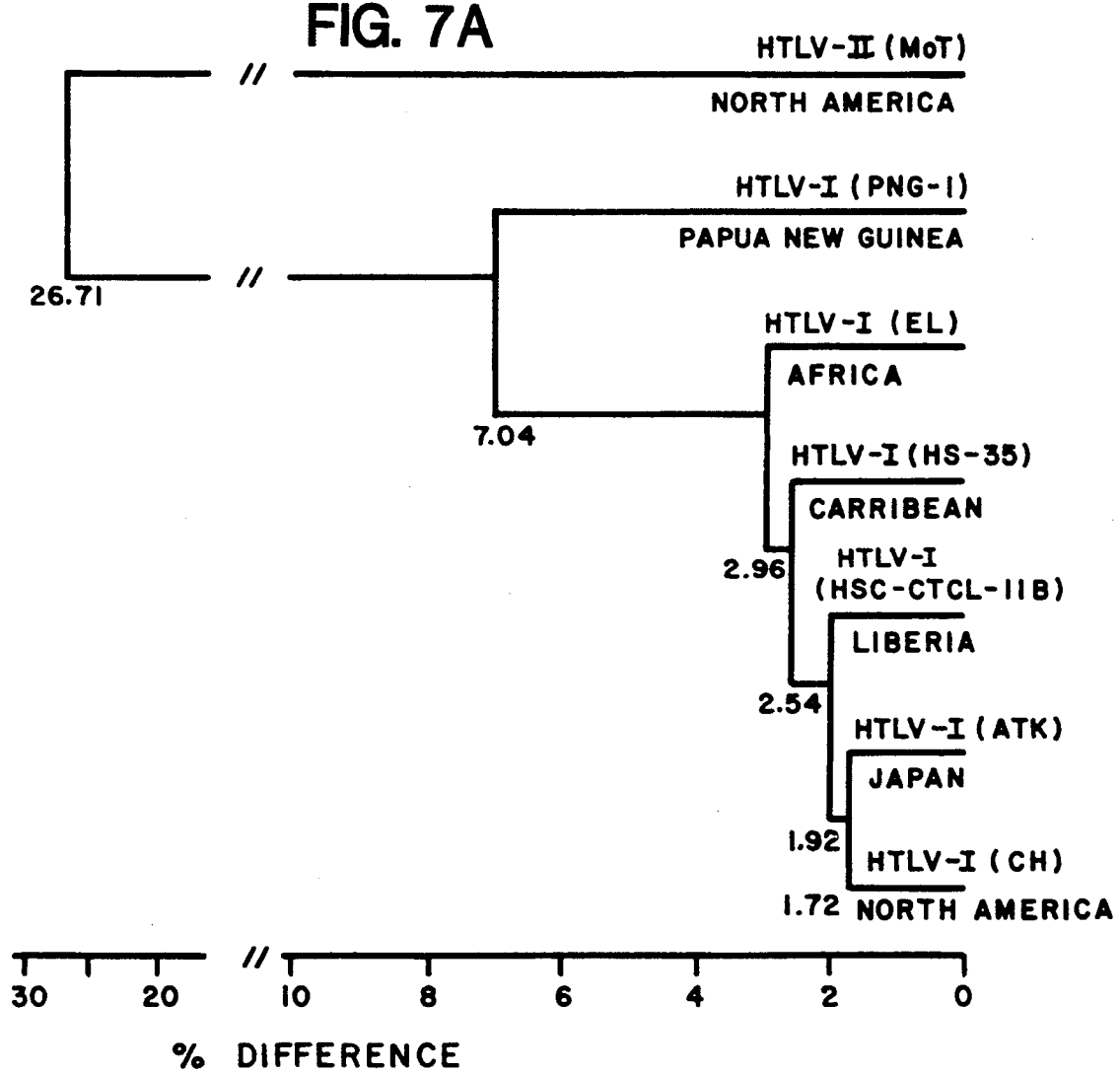
FIGS. 7A to 7B show dendrograms evolutionary trees for the HTLV/STLV family of retroviruses.

Since the evolutionary branching pattern of these related retroviruses differs from the pattern of the host species, there has been interspecies transmission between humans and nonhuman primates (Ina et al., J. Mol. Evol. 1990; 31:493–499). It has also been demonstrated that the HTLV family evolved with a relatively constant rate and that HTLV-II diverged from the common ancestor of STLV-I and HTLV-I (Ina et al., J. Mol. Evol. 1990; 31:493–499). From a relative rate standpoint (Sarich et al., Science 1990; 179:1144–1147) the present data are consistent with this interpretation. In FIG. 7A, the four sequenced regions (pol, pX, gp21 and gp46) were compared and the divergence pattern showed that PNG-1 diverged from a common ancestor of HTLV-I prior to strains from Africa (EL) (Paine et al., Virology 1991; 182:111–123), the Caribbean (HS-35) (Malik et al., J. Gen. Virol. 1988; 69:1695–1710), Liberia (HSC-CTCL-11B) (Ehrlich et al., Am. J. Hematol. 1989; 30:128–139), Japan (ATK) (Seiki et al., PNAS USA 1983; 80:3618–3622), and North America (CH) (Paine et al., Virology 1991; 182:111–123) and that PNG-1 is more closely related to HTLV-II than these other isolates. HTLV-I may have originated at the same time or prior to the time when the ancestors of these ancient Hagahai people of Papua, New Guinea became isolated.

Figure 7B:
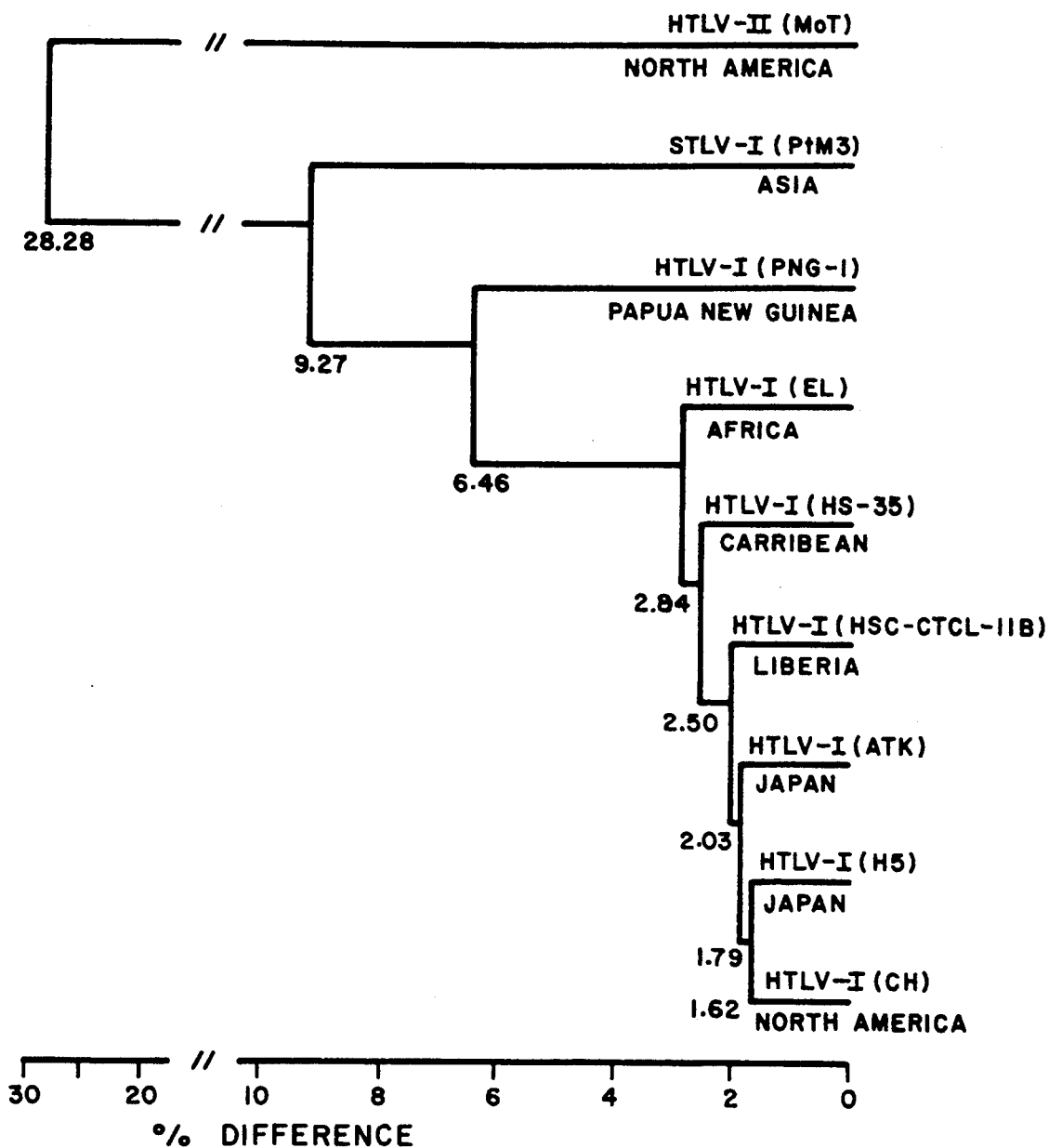

A dendrogram, constructed exclusive of the pol region (FIG. 7B permits inclusion of STLV-I (Watanabe et al., Virology 1985; 144:59–64) and an isolate from a Japanese HTLV-I-associated myelopathy patient (H5) (Tsujimoto et al., Mol. Biol. Med. 1988; 5:29–42). The degree of divergence for PNG-1 decreased slightly relative to other HTLV-I isolates, but now an Asian subtype of STLV-I can be seen branching from HTLV-II prior to PNG-1. The Asian subtype of STLV-I varied from prototype HTLV-I by 10% and at the same time the African subtype of STLV-I varies by only 5% (Watanabe et al., Virology 1986; 143:385–388). These estimates are based on comparisons of a highly variable region of HTLV, the LTR. When more conservative regions are analyzed, the Asian subtype of STLV-I varied by almost 10% and PNG-1 varied by approximately 6.5%. If one extrapolated the differences in the African subtype of STLV-I onto this dendrogram, it would branch off after PNG-1, implying that interspecies transmission between humans and nonhuman primates of African origin continued to occur after the Asian subtype of STLV-I and PNG-1 branched away from the rest of what is HTLV-I.

The dendrograms seem to reflect the entire genome, as the divergence pattern for the isolates other than PNG-1 is in complete agreement with dendrograms created for the HTLV family based on sequences of full-length clones and of clones of several kilobases in length.

The absence of nonhuman primates in Papua New Guinea and the Solomon Islands, both currently and in prehistoric times, indicates either that interspecies transmission occurred long before the introduction of HTLV-I in Melanesia or that HTLV-I Melanesia did not originate in monkeys. However, if the proto-Melanesian HTLV-I strain had its origin in nonhuman primates in Africa, the early and prolonged isolation of Melanesian populations are likely to have resulted in the evolution of a markedly different variant, since even the most divergent HTLV-I strains from Africa show $\geq 97\%$ sequence identity with prototype HTLV-I (Paine et al., Virology 1991; 182:111–123).

All publications cited hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Pro Ile Leu Ser Phe Tyr Ser Pro Ser Cys Cys Thr
1                5                              10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu Ala Ile Gly Thr Gly Ile Ala Gly Gly Ile Thr
1                5                              10

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCGGCCTCAC AATCCCGTTC CCGC                          24

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TGGCGGTCTG GCTAGTCTCC 20

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AAACGTGGGA ATTAGTGATG TTTA 24

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CTTGTAGCGC CTTGCATAAT CC 22

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CAGACGAGGC CTTGATCTCC 20

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CCGGCCTCAC AATCCCGTTC CCGC 24

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TGGCGGTCTG GCTAGTCTCC 20

( 2 ) INFORMATION FOR SEQ ID NO:10:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:10:

AAACGTGGGA ATTAGTGATG TTTA    24

( 2 ) INFORMATION FOR SEQ ID NO:11:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:11:

CTTGTAGCGC CTTGCATAAT CC    22

( 2 ) INFORMATION FOR SEQ ID NO:12:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:12:

ACAGGTACCT GCAGATCTAG A    21

( 2 ) INFORMATION FOR SEQ ID NO:13:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:13:

TACGAGCTCG CGAATTCATG A    21

( 2 ) INFORMATION FOR SEQ ID NO:14:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:14:

TTTGAGCGGC CGCTCAAGCT ATAGTCTCCT CCCCTG    36

( 2 ) INFORMATION FOR SEQ ID NO:15:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:15:

ACTTAGAATT CGGAGGTGTC GTAGCTGACG GAGG  34

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CAGACGAGGC CTTGATCTCC  20

( 2 ) INFORMATION FOR SEQ ID NO:17:

( i ) SEQUENCE CHARACTERISTICS:
        ( A ) LENGTH: 159 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 19..138

( x i ) SEQUENCE DESCRIPTION: SEQ ID NO:17:

```
CGGATACCCA GTCTACGT GTT TGG AGA CTG TGT ACA AGG CGA CTG GTG CCC    51
                    Val Trp Arg Leu Cys Thr Arg Arg Leu Val Pro
                     1            5                      10

CAT CTC TGG GGG ACT ATG TTC GGC CCG CCT ACA TCG TCA CGC CCT ACT    99
His Leu Trp Gly Thr Met Phe Gly Pro Pro Thr Ser Ser Arg Pro Thr
             15              20                  25

GGC CAC CTG TCC AGA GCA TCA GAT CAC CTG GGA CCC CAT CGATGGACGC    148
Gly His Leu Ser Arg Ala Ser Asp His Leu Gly Pro His
         30              35              40

GTTATCGGCT C                                                      159
```

( 2 ) INFORMATION FOR SEQ ID NO:18:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Val Trp Arg Leu Cys Thr Arg Arg Leu Val Pro His Leu Trp Gly Thr
 1            5                      10                      15

Met Phe Gly Pro Pro Thr Ser Ser Arg Pro Thr Gly His Leu Ser Arg
             20                  25                  30

Ala Ser Asp His Leu Gly Pro His
         35              40
```

( 2 ) INFORMATION FOR SEQ ID NO:19:

( i ) SEQUENCE CHARACTERISTICS:
        ( A ) LENGTH: 186 base pairs
        ( B ) TYPE: nucleic acid
        ( C ) STRANDEDNESS: single
        ( D ) TOPOLOGY: linear (ii) MOLECULE TYPE: cDNA (ix) FEATURE:
    (A) NAME/KEY: CDS
    (B) LOCATION: 22..162

(xi) SEQUENCE DESCRIPTION: SEQ ID NO:19:

```
CCCTACAATC CAACCAGCTC A GGA CTT GTA GAA CGC TCT AAT GGC ATT CTT        51
                        Gly Leu Val Glu Arg Ser Asn Gly Ile Leu
                         1               5                    10

AAA ACC CTA TTA TAT AAG TAC TTT ACT GAC AAA CCC GAC CTA CCC ATG         99
Lys Thr Leu Leu Tyr Lys Tyr Phe Thr Asp Lys Pro Asp Leu Pro Met
             15                  20                      25

GAT AAT GCT CTA TCC ATA GCC CTA TGG ACA ATC AAC CAC CTG AAT GTG        147
Asp Asn Ala Leu Ser Ile Ala Leu Trp Thr Ile Asn His Leu Asn Val
             30                  35                      40

TTA ACC AAC TGC CAC AAAACCCGAT GGCAGCTTCA CCAC                         186
Leu Thr Asn Cys His
             45
```

(2) INFORMATION FOR SEQ ID NO:20:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:20:

```
Gly Leu Val Glu Arg Ser Asn Gly Ile Leu Lys Thr Leu Leu Tyr Lys
 1               5                  10                  15

Tyr Phe Thr Asp Lys Pro Asp Leu Pro Met Asp Asn Ala Leu Ser Ile
             20                  25                  30

Ala Leu Trp Thr Ile Asn His Leu Asn Val Leu Thr Asn Cys His
             35                  40                  45
```

(2) INFORMATION FOR SEQ ID NO:21:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 32..205

(xi) SEQUENCE DESCRIPTION: SEQ ID NO:21:

```
CCACAAAAAT CTACTCAAAA TTGCGCAGTA T GCT GCC CAG AAC AGA CGA GGC         52
                                  Ala Ala Gln Asn Arg Arg Gly
                                   1               5

CTT GAT CTC CTG TTC TGG GAG CAA GGA GGA TTA TGC AAA GCA TTA CAA       100
Leu Asp Leu Leu Phe Trp Glu Gln Gly Gly Leu Cys Lys Ala Leu Gln
             10                  15                      20

GAA CAG TGC CGT TTT CCG AAT ATT ACC AAT TCC CAT GTC CCA ATA CTA       148
Glu Gln Cys Arg Phe Pro Asn Ile Thr Asn Ser His Val Pro Ile Leu
         25                  30                  35

CAA GAA AGA CCC CCC CTT GAG AAT CGA GTC CTG ACT GGC TGG GGC CTT       196
Gln Glu Arg Pro Pro Leu Glu Asn Arg Val Leu Thr Gly Trp Gly Leu
 40                  45                  50                  55

AAC TGG GAC CTTGGCCTCT CACAGTGGGC TCGAGAGGCC                          235
Asn Trp Asp
```

(2) INFORMATION FOR SEQ ID NO:22:

(i) SEQUENCE CHARACTERISTICS:
  (A) LENGTH: 58 amino acids
  (B) TYPE: amino acid
  (D) TOPOLOGY: linear (ii) MOLECULE TYPE: protein (xi) SEQUENCE DESCRIPTION: SEQ ID NO:22:

```
Ala Ala Gln Asn Arg Arg Gly Leu Asp Leu Leu Phe Trp Glu Gln Gly
 1               5                  10                  15

Gly Leu Cys Lys Ala Leu Gln Glu Gln Cys Arg Phe Pro Asn Ile Thr
            20                  25                  30

Asn Ser His Val Pro Ile Leu Gln Glu Arg Pro Pro Leu Glu Asn Arg
        35                  40                  45

Val Leu Thr Gly Trp Gly Leu Asn Trp Asp
    50                  55
```

(2) INFORMATION FOR SEQ ID NO:23:

(i) SEQUENCE CHARACTERISTICS:
  (A) LENGTH: 369 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 20..343

(xi) SEQUENCE DESCRIPTION: SEQ ID NO:23:

```
TTTATTCTTC CAGTTCTGC CCC CTC ATC TTC GGT GAT TAC AGC CCC AGC TGC        52
                     Pro Leu Ile Phe Gly Asp Tyr Ser Pro Ser Cys
                      1               5                      10

TGT ACT CTC ACA ATT GGA GTC TCC TCA TAC CAC TCT AAA CCC TGC AAT        100
Cys Thr Leu Thr Ile Gly Val Ser Ser Tyr His Ser Lys Pro Cys Asn
             15                  20                  25

CCT GCC CAG CCA GTT TGT TCG TGG ACC CTC GAC CTG CTG GCC CTT TCA        148
Pro Ala Gln Pro Val Cys Ser Trp Thr Leu Asp Leu Leu Ala Leu Ser
         30                  35                  40

GCA GAT CAG GCC CTA CAG CCC CCC TGC CCT AAC CTA GTA AGT TAC TCC        196
Ala Asp Gln Ala Leu Gln Pro Pro Cys Pro Asn Leu Val Ser Tyr Ser
     45                  50                  55

AGC TAC CAT GCC ACC TAT TCC CTA TAT CTA TTC CCT CAT TGG ACT AAG        244
Ser Tyr His Ala Thr Tyr Ser Leu Tyr Leu Phe Pro His Trp Thr Lys
 60                  65                  70                  75

AAG CCA AAC CGA AAT GGC GGA GGC TAT TAT TCA GCC TCT TAT TCA GAC        292
Lys Pro Asn Arg Asn Gly Gly Gly Tyr Tyr Ser Ala Ser Tyr Ser Asp
             80                  85                  90

CCT TGT TCC TTA AAG TGC CCA TAC CTG GGG TGC CAA TCA TGG ACC TGC        340
Pro Cys Ser Leu Lys Cys Pro Tyr Leu Gly Cys Gln Ser Trp Thr Cys
         95                 100                 105

CCC TATACAGGAG CCGTCTCCAG CCCCTA                                       369
Pro
```

(2) INFORMATION FOR SEQ ID NO:24:

(i) SEQUENCE CHARACTERISTICS:
  (A) LENGTH: 108 amino acids
  (B) TYPE: amino acid
  (D) TOPOLOGY: linear (ii) MOLECULE TYPE: protein (xi) SEQUENCE DESCRIPTION: SEQ ID NO:24:

| Pro | Leu | Ile | Phe | Gly | Asp | Tyr | Ser | Pro | Ser | Cys | Cys | Thr | Leu | Thr | Ile |
|---|---|---|---|---|---|---|---|---|---|---|---|---|---|---|---|
| 1 | | | | 5 | | | | 10 | | | | | | 15 | |

| Gly | Val | Ser | Ser | Tyr | His | Ser | Lys | Pro | Cys | Asn | Pro | Ala | Gln | Pro | Val |
|---|---|---|---|---|---|---|---|---|---|---|---|---|---|---|---|
| | | | 20 | | | | | 25 | | | | | 30 | | |

| Cys | Ser | Trp | Thr | Leu | Asp | Leu | Leu | Ala | Leu | Ser | Ala | Asp | Gln | Ala | Leu |
|---|---|---|---|---|---|---|---|---|---|---|---|---|---|---|---|
| | | | 35 | | | | 40 | | | | | 45 | | | |

| Gln | Pro | Pro | Cys | Pro | Asn | Leu | Val | Ser | Tyr | Ser | Ser | Tyr | His | Ala | Thr |
|---|---|---|---|---|---|---|---|---|---|---|---|---|---|---|---|
| | 50 | | | | | 55 | | | | | 60 | | | | |

| Tyr | Ser | Leu | Tyr | Leu | Phe | Pro | His | Trp | Thr | Lys | Lys | Pro | Asn | Arg | Asn |
|---|---|---|---|---|---|---|---|---|---|---|---|---|---|---|---|
| 65 | | | | | 70 | | | | | 75 | | | | | 80 |

| Gly | Gly | Gly | Tyr | Tyr | Ser | Ala | Ser | Tyr | Ser | Asp | Pro | Cys | Ser | Leu | Lys |
|---|---|---|---|---|---|---|---|---|---|---|---|---|---|---|---|
| | | | | 85 | | | | | 90 | | | | | 95 | |

| Cys | Pro | Tyr | Leu | Gly | Cys | Gln | Ser | Trp | Thr | Cys | Pro |
|---|---|---|---|---|---|---|---|---|---|---|---|
| | | | 100 | | | | | 105 | | | |

(2) INFORMATION FOR SEQ ID NO:25:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

| | | | | | |
|---|---|---|---|---|---|
| TCATAACTCC | CTCATCCTGC | CCCCCTTTTC | CTTGTCACCT | GTTCCCACCC | TAGGATCCCG | 60 |
| CTCCCGCCGA | GCGGTACCGG | TGGCGGTCTG | GCTTGTCTCC | GCCCTGGCCA | TGGGAGCCGG | 120 |
| AGTGGCTGGC | GGGATTACCG | GCTCCATGTC | CCTCGCCTCA | GGAAAGAGCC | TCCTACATGA | 180 |
| GGTGGACAAA | GATATTTCCC | AGTTAACTCA | AGCAATAGTC | AAAAACCACA | AAAATCTACT | 240 |
| CAAAATTGCG | CAGTATGCTG | CCCAGAACAG | ACGAGGCCTT | GATCTCCTGT | TCTGGGAGCA | 300 |
| AGGAGGATTA | TGCAAAGCAT | TACAAGAACA | GTGCTGTTTT | CTGAATATTA | CTAATTCCCA | 360 |
| TGTCTCAATA | CTACAAGAAA | GACCCCCCCT | TGAGAATCGA | GTCCTGACTG | GCTGGGGCCT | 420 |
| TAACTGGGAC | CTTGGCCTCT | CACAGTGGGC | TCGAGAGGCC | TTACAAACTG | GAATCACCCT | 480 |
| TGTTGCGCTA | CTCCTTCTTG | TTATCCTTGC | AGGACCATGC | | | 520 |

(2) INFORMATION FOR SEQ ID NO:26:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

| His | Asn | Ser | Leu | Ile | Leu | Pro | Pro | Phe | Ser | Leu | Ser | Pro | Val | Pro | Thr |
|---|---|---|---|---|---|---|---|---|---|---|---|---|---|---|---|
| 1 | | | | 5 | | | | | 10 | | | | | 15 | |

| Leu | Gly | Ser | Arg | Ser | Arg | Arg | Ala | Val | Pro | Val | Ala | Val | Trp | Leu | Val |
|---|---|---|---|---|---|---|---|---|---|---|---|---|---|---|---|
| | | | 20 | | | | | 25 | | | | | 30 | | |

| Ser | Ala | Leu | Ala | Met | Gly | Ala | Gly | Val | Ala | Gly | Gly | Ile | Thr | Gly | Ser |
|---|---|---|---|---|---|---|---|---|---|---|---|---|---|---|---|
| | | | 35 | | | | | 40 | | | | | 45 | | |

| Met | Ser | Leu | Ala | Ser | Gly | Lys | Ser | Leu | Leu | His | Glu | Val | Asp | Lys | Asp |
|---|---|---|---|---|---|---|---|---|---|---|---|---|---|---|---|
| | 50 | | | | | 55 | | | | | 60 | | | | |

| Ile | Ser | Gln | Leu | Thr | Gln | Ala | Ile | Val | Lys | Asn | His | Lys | Asn | Leu | Leu |
|---|---|---|---|---|---|---|---|---|---|---|---|---|---|---|---|
| 65 | | | | | 70 | | | | | 75 | | | | | 80 |

| Lys | Ile | Ala | Gln | Tyr | Ala | Ala | Gln | Asn | Arg | Arg | Gly | Leu | Asp | Leu | Leu |

|  |  |  |  |  |  |  |  |  |  |  |  |  |  |  |
|---|---|---|---|---|---|---|---|---|---|---|---|---|---|---|
|  |  |  |  | 85 |  |  |  | 90 |  |  |  | 95 |  |  |
| Phe | Trp | Glu | Gln<br>100 | Gly | Gly | Leu | Cys | Lys<br>105 | Ala | Leu | Gln | Glu | Gln<br>110 | Cys | Cys |
| Phe | Leu | Asn<br>115 | Ile | Thr | Asn | Ser | His<br>120 | Val | Ser | Ile | Leu | Gln<br>125 | Glu | Arg | Pro |
| Pro | Leu<br>130 | Glu | Asn | Arg | Val | Leu<br>135 | Thr | Gly | Trp | Gly | Leu<br>140 | Asn | Trp | Asp | Leu |
| Gly<br>145 | Leu | Ser | Gln | Trp | Ala<br>150 | Arg | Glu | Ala | Leu | Gln<br>155 | Thr | Gly | Ile | Thr | Leu<br>160 |
| Val | Ala | Leu | Leu | Leu<br>165 | Leu | Val | Ile | Leu | Ala<br>170 | Gly | Pro | Cys |  |  |  |

What is claimed is:

1. A cell line, designated papua New Guinea-1(pNG-1) ATCC CRL 10528.

2. A viral preparation comprising the HTLV-I-variant in the cell line ATCC CRL 10528 of claim 1.

3. A bioassay for the diagnosis of infection with PNG-1 variant comprising the steps of:
   i) fixing said cell according to claim 1 to a solid support;
   ii) contacting said cell with a biological sample from a human suspected of being infected; and
   iii) detecting the presence or absence of a complex formed between protein of said cell and antibodies specific therefor present in said sample.

4. The bioassay according to claim 3 further comprising permeabilizing said fixed cell prior to contacting said cell with a biological sample.

5. A bioassay for the diagnosis of infection with PNG-1 variant comprising the steps of:
   i) preparing a lysate from said cell according to claim 1;
   ii) contacting said lysate with a biological sample from a human suspected of being infected, under conditions such that a complex is formed between protein of said lysate and antibodies specific therefor present in said sample; and
   iii) detecting the presence or absence of said complex.

* * * * *